US011627932B2

(12) United States Patent
Neben et al.

(10) Patent No.: US 11,627,932 B2
(45) Date of Patent: Apr. 18, 2023

(54) METHODS AND APPARATUSES FOR ULTRASOUND IMAGING OF LUNGS

(71) Applicant: BFLY OPERATIONS, INC., Burlington, MA (US)

(72) Inventors: Abraham Neben, Guilford, CT (US); Karl Thiele, St. Petersburg, FL (US); Brenda Gonyeau, Feeding Hills, MA (US)

(73) Assignee: BFLY OPERATIONS, INC., Burlington, MA (US)

( * ) Notice: Subject to any disclaimer, the term of this patent is extended or adjusted under 35 U.S.C. 154(b) by 45 days.

(21) Appl. No.: 16/532,784

(22) Filed: Aug. 6, 2019

(65) Prior Publication Data
US 2020/0046314 A1 Feb. 13, 2020

Related U.S. Application Data

(60) Provisional application No. 62/715,306, filed on Aug. 7, 2018.

(51) Int. Cl.
*A61B 8/08* (2006.01)

(52) U.S. Cl.
CPC .............. *A61B 8/08* (2013.01); *A61B 8/5223* (2013.01); *A61B 8/5238* (2013.01)

(58) Field of Classification Search
CPC ....... A61B 8/08; A61B 8/5223; A61B 8/5238; A61B 5/08–097; A61B 8/54; G01S 15/8952
See application file for complete search history.

(56) References Cited

U.S. PATENT DOCUMENTS 4,974,558 A * 12/1990 Katakura ................ A61B 8/14
600/447
5,315,999 A * 5/1994 Kinicki ............... G01S 7/52073
600/443

(Continued)

FOREIGN PATENT DOCUMENTS

CN 107357435 A * 11/2017
WO WO-2008073560 A2 * 6/2008 ............. A61B 8/469
WO WO 2017/222964 A1 12/2017

OTHER PUBLICATIONS

CN-107357435-A (Year: 2017).*

(Continued)

*Primary Examiner* — Joel Lamprecht
*Assistant Examiner* — Nyrobi Celestine
(74) *Attorney, Agent, or Firm* — Osha Bergman Watanabe & Burton LLP

(57) ABSTRACT

Aspects of the technology described herein relate to ultrasound imaging of lungs. An ultrasound device may be configured with a set of parameter values associated with a shallow lung imaging mode. A selection of a change in imaging depth may be received. If the selected imaging depth is greater than or equal to a threshold imaging depth, the ultrasound device may be configured with a set of parameter values associated with a deep lung imaging mode. The set of parameter values associated with the shallow lung imaging mode may be optimized for imaging lung sliding and the set of parameter values associated with the deep lung imaging mode may be optimized for imaging A lines and B lines.

23 Claims, 18 Drawing Sheets

(56) References Cited

U.S. PATENT DOCUMENTS

| | | | | |
|---|---|---|---|---|
| 6,132,374 | A * | 10/2000 | Hossack | A61B 8/00 600/443 |
| 7,852,461 | B2 * | 12/2010 | Yahav | H04N 13/239 356/3.08 |
| 9,521,991 | B2 | 12/2016 | Rothberg et al. | |
| 9,592,030 | B2 | 3/2017 | Rothberg et al. | |
| 10,751,025 | B2 * | 8/2020 | Rajagopal | A61B 8/4477 |
| 2002/0111568 | A1 * | 8/2002 | Bukshpan | A61B 8/4488 601/2 |
| 2008/0021326 | A1 | 1/2008 | Bakircioglu et al. | |
| 2009/0069682 | A1 * | 3/2009 | Hastings | G01S 7/52084 600/443 |
| 2009/0182237 | A1 * | 7/2009 | Angelsen | G01S 15/8918 600/459 |
| 2010/0128947 | A1 * | 5/2010 | Vaidya | A61B 6/032 382/131 |
| 2011/0046484 | A1 * | 2/2011 | Adams | G01S 15/8918 600/440 |
| 2011/0055447 | A1 | 3/2011 | Costa | |
| 2013/0259341 | A1 | 10/2013 | Mountney et al. | |
| 2013/0281855 | A1 * | 10/2013 | Baba | A61B 8/5207 600/441 |
| 2015/0297164 | A1 * | 10/2015 | Dankerl | A61B 6/5217 600/425 |
| 2016/0310110 | A1 * | 10/2016 | Dodd | A61B 8/54 |
| 2017/0071579 | A1 * | 3/2017 | Ko | A61B 8/4254 |
| 2017/0360397 | A1 | 12/2017 | Rothberg et al. | |
| 2017/0360401 | A1 | 12/2017 | Rothberg et al. | |
| 2017/0360402 | A1 | 12/2017 | De Jonge et al. | |
| 2017/0360403 | A1 | 12/2017 | Rothberg et al. | |
| 2017/0360404 | A1 | 12/2017 | Gafner et al. | |
| 2017/0360411 | A1 | 12/2017 | Rothberg et al. | |
| 2017/0360412 | A1 | 12/2017 | Rothberg et al. | |
| 2017/0360415 | A1 | 12/2017 | Rothberg et al. | |
| 2018/0085096 | A1 * | 3/2018 | Brandl | A61B 8/5207 |
| 2018/0220995 | A1 | 8/2018 | Pelissier et al. | |
| 2018/0344293 | A1 * | 12/2018 | Raju | A61B 8/085 |
| 2019/0142388 | A1 | 5/2019 | Gonyeau et al. | |
| 2019/0307428 | A1 | 10/2019 | Silberman et al. | |

OTHER PUBLICATIONS

International Preliminary Report on Patentability dated Feb. 18, 2021 in connection with International Application No. PCT/US2019/045256.

International Search Report and Written Opinion dated Oct. 24, 2019 in connection with International Application No. PCT/US2019/045256.

Lichtenstein, Lung ultrasound in the critically ill. Annals of Intensive Care. 2014; 4:1, 12 pages.

* cited by examiner

METHODS AND APPARATUSES FOR ULTRASOUND IMAGING OF LUNGS

CROSS-REFERENCE TO RELATED APPLICATIONS

This application claims the benefit under 35 U.S.C. § 119(e) of U.S. Provisional Application Ser. No. 62/715,306, titled "METHODS AND APPARATUSES FOR ULTRASOUND IMAGING OF LUNGS," filed on Aug. 7, 2018, which is incorporated herein by reference in its entirety.

FIELD

Generally, the aspects of the technology described herein relate to ultrasound imaging of lungs.

BACKGROUND

Ultrasound probes may be used to perform diagnostic imaging and/or treatment, using sound waves with frequencies that are higher than those audible to humans. Ultrasound imaging may be used to see internal soft tissue body structures, for example to find a source of disease or to exclude pathology. When pulses of ultrasound are transmitted into tissue (e.g., by using an ultrasound probe), sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound probes, including real-time images. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect, an apparatus includes a processing device in operative communication with an ultrasound device, the processing device configured to configure the ultrasound device with a set of parameter values associated with a first imaging mode, receive a selection of an imaging depth determine that the selected imaging depth is greater than a threshold imaging depth or determine that the selected imaging depth is greater than or equal to the threshold imaging depth, and configure the ultrasound device with a set of parameter values associated with a second imaging mode.

In some embodiments, the first imaging mode comprises a shallow lung imaging mode and the second imaging mode comprises a deep lung imaging mode. In some embodiments, the first imaging mode is associated with imaging depths that are smaller than or equal to the threshold imaging depth and the second imaging mode is associated with imaging depths that are larger than the threshold imaging depth, or the first imaging mode is associated with imaging depths that are smaller than the threshold imaging depth and the second imaging mode is associated with imaging depths that are larger than or equal to the threshold imaging depth. In some embodiments, the threshold imaging depth is between approximately 4 cm and 8 cm.

In some embodiments, the set of parameter values associated with the first imaging mode comprises a peak frequency of transmitted ultrasound between approximately 5 MHz and 10 MHz. In some embodiments, the set of parameter values associated with the second imaging mode comprises a peak frequency of transmitted ultrasound between approximately 2 MHz and 5 MHz.

In some embodiments, the set of parameter values associated with the first imaging mode comprises a receive frequency between approximately 5 MHz and 10 MHz. In some embodiments, the set of parameter values associated with the second imaging mode comprises a receive frequency between approximately 2 MHz and 5 MHz.

In some embodiments, the set of parameter values associated with the first imaging mode comprises a virtual apex greater than or equal to approximately 10 cm above a skin line of a subject being imaged. In some embodiments, the set of parameter values associated with the second imaging mode comprises a virtual apex between approximately 0 cm and 5 cm above a skin line of a subject being imaged.

In some embodiments, the set of parameter values associated with the first imaging mode comprises an image field of view angle between approximately 0 and 20 degrees around a virtual apex. In some embodiments, the set of parameter values associated with the second imaging mode comprises an image field of view angle between approximately 40 degrees and 90 degrees around a virtual apex.

In some embodiments, the set of parameter values associated with the first imaging mode comprises an instantaneous transmit aperture between approximately 4 mm and 8 mm. In some embodiments, the set of parameter values associated with the second imaging mode comprises an instantaneous transmit aperture between approximately 12 mm and 20 mm.

In some embodiments, the set of parameter values associated with the first imaging mode comprises a linear ultrasound image format. In some embodiments, the set of parameter values associated with the second imaging mode comprises a sector ultrasound image format.

In some embodiments, the set of parameter values associated with the first imaging mode comprises time gain compensation gain values of approximately 0 dB, −8 dB, and −2 dB at respective control points of approximately 0 cm, 3 cm, and 6 cm. In some embodiments, the set of parameter values associated with the second imaging mode comprises time gain compensation gain values of approximately 0 dB, 0 dB, and 5 dB at respective control points of approximately 0 cm, 3 cm, and 6 cm.

In some embodiments, the set of parameter values associated with the first imaging mode is optimized for imaging lung sliding. In some embodiments, the set of parameter values associated with the second imaging mode is optimized for imaging A lines and B lines.

In some embodiments, the processing device is further configured to receive a user selection of a lung imaging preset option. In some embodiments, the processing device is further configured to automatically determine that lung imaging is being performed by the ultrasound device. In some embodiments, the processing device is configured, when automatically determining that lung imaging is being performed by the ultrasound device, to receive ultrasound data from the ultrasound device and determine that the ultrasound data was collected from lungs. In some embodiments, the processing device is configured, when determining that the ultrasound data was collected from the lungs, to input the ultrasound data to a statistical model trained to accept inputted ultrasound data and determine an anatomical region where the inputted ultrasound data was collected. In some embodiments, the processing device is configured, when automatically determining that lung imaging is being performed by the ultrasound device, to receive an optical image of the ultrasound device and the subject and determine that the ultrasound device is located at the subject's lungs. In some embodiments, the processing device is configured, when determining that the ultrasound device is located at the subject's lungs, to input the ultrasound data to a statistical model trained to accept an inputted optical image depicting an ultrasound device and a subject and determine an anatomical region on the depicted subject where the depicted ultrasound device is located. In some embodiments, the optical image is collected by a camera on the processing device.

In some embodiments, the processing device is further configured to receive a second selection of an imaging depth, determine that the second selected imaging depth is less than or equal to the threshold imaging depth or the second selected imaging depth is less than the threshold imaging depth, and configure the ultrasound device with the set of parameter values associated with the first imaging mode.

Some aspects include at least one non-transitory computer-readable storage medium storing processor-executable instructions that, when executed by at least one processor, cause the at least one processor to perform the above aspects and embodiments. Some aspects include a method to perform the actions that the apparatus is configured to perform.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Figure 1:
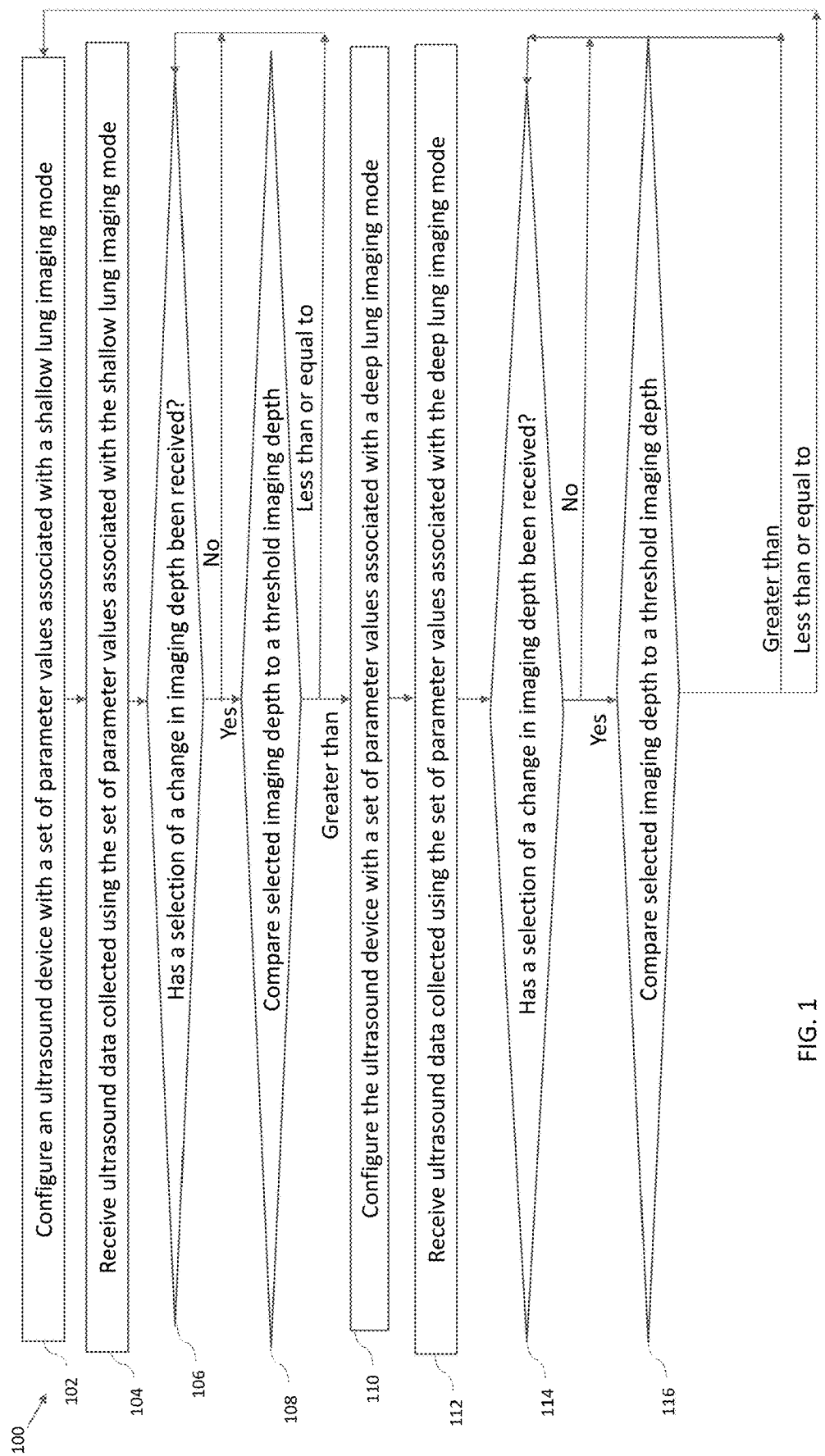
FIG. 1 illustrates an example process for ultrasound imaging of lungs, in accordance with certain embodiments described herein.

Ultrasound waves are strongly reflected by the air-tissue interface at the edge of the lung (the pleura), such that they typically do not penetrate into the lungs. Thus, it generally is not possible to reconstruct, based on reflected ultrasound waves, an ultrasound image of the lungs that depicts the physical structure of the lungs in the same way that ultrasound images of other anatomical structures (such as the heart, for example) can be formed. However, reflections of ultrasound waves by the pleura typically do produce predictable artifacts in reconstructed ultrasound images. These artifacts include lung sliding, A lines, and B lines. Lung sliding is an artifact produced when two membranes of the lung slide against one other during breathing, thereby creating an interference pattern which in turn produces a shimmering effect along the pleural line in reconstructed images. While the pleural line is the first reflection of ultrasound waves off the lungs, higher order reflections appear as additional horizontal lines (A lines) below the pleural line. If there is fluid between the two membranes, the fluid may generate artifacts called B lines which appear as radial lines extending from the pleural line deep into the image. These artifacts may be used for diagnosis. For example, the BLUE (Bedside Lung Ultrasound in Emergency) protocol is a fast protocol that uses ultrasound imaging of the lungs to diagnose acute respiratory failure. In particular, the BLUE protocol uses detection of lung sliding, A lines, and B lines in a decision tree for determining whether a patient may have pulmonary edema, pulmonary embolism, pneumonia, chronic obstructive pulmonary disease (COPD), asthma, or pneumothorax. Further description of the BLUE protocol may be found in Lichtenstein, Daniel A, "Lung ultrasound in the critically ill," *Annals of intensive care* 4.1 (2014): 1, the content of which is incorporated by reference herein in its entirety.

The imaging requirements for detecting lung sliding versus detecting A lines and B lines are often different. Detecting lung sliding generally requires high resolution imaging with as little spatial and time averaging as possible. This enables ultrasound images to show detail and movement of the shimmering pattern characteristic of lung sliding. High resolution imaging generally requires higher ultrasound transmit frequency (i.e., the frequency content of transmitted ultrasound energy). In turn, using higher frequency ultrasound may require shallower imaging (i.e., smaller imaging depth) as higher frequency ultrasound generally does not penetrate as far into tissue as lower frequency ultrasound due to attenuation. By contrast, detecting A lines generally requires high penetration of ultrasound pulses as A line artifacts are produced due to ultrasound pulses traveling multiple round trips between the transducer surface and the pleural line (i.e., large propagation distance). A line artifacts thereby manifest as copies of the pleural line when large imaging depths are used. Detecting B lines also generally requires high penetration of ultrasound pulses in order to verify that the B lines extend to the bottom of the ultrasound image. This may help to distinguish B lines from other artifacts such as comet-tail artifacts. High penetration of ultrasound pulses generally requires lower ultrasound transmit frequency, as lower frequency ultrasound is generally able to penetrate deeper than higher frequency ultrasound. Thus, detecting lung sliding may require high frequency/low depth imaging while detecting A lines and B lines may require low frequency/high depth imaging.

Typical ultrasound systems include multiple ultrasound probes, each of which is typically optimized for a certain frequency range. To use such ultrasound systems to image lung sliding, a user typically uses one ultrasound probe optimized for a higher frequency range (e.g., a linear transducer array probe). In order to image A lines and B lines, the user typically uses a different ultrasound probe optimized for a lower frequency range (e.g., a sector transducer array probe).

The inventors have recognized that it may be inefficient and/or difficult to require a user to use two different ultrasound probes to image the same anatomical structure, such as the lungs. Accordingly, the inventors have developed technology that facilitates imaging of lung sliding, A lines, and B lines, with a single ultrasound device. (As referred to herein, a single ultrasound device should be understood to mean an ultrasound device having a single transducer array.) In particular, the ultrasound device may be configured with imaging parameters appropriate either for detecting lung sliding or for detecting A lines and B lines. Because detecting lung sliding generally requires smaller imaging depth and detecting A lines and B lines generally requires greater imaging depth, the inventors have recognized that a user may indicate whether imaging of lung sliding or A lines and B lines is desired based on the selected imaging depth. If the user selects an imaging depth shallower than or equal to a threshold depth, the ultrasound device may be automatically configured with imaging parameters appropriate for detecting lung sliding. If the user selects an imaging depth deeper than a threshold depth, the ultrasound device may be automatically configured with imaging parameters appropriate for detecting A lines and B lines. It should be appreciated that while the above description has described ultrasound transmit frequency and imaging depth as imaging parameters that may be varied based on whether detecting lung sliding or A lines and B lines is desired, other imaging parameters may also be varied, as described below.

As described above, detecting lung sliding, A lines, and B lines may require an ultrasound system that enables imaging across a broad frequency range, as detecting lung sliding may require high frequencies while detecting A lines and B lines may require low frequencies. Typical ultrasound systems use ultrasound transducers based on piezoelectric materials. Piezoelectric materials generally have narrow bandwidths, and therefore in order to enable ultrasound imaging across a broad frequency range, such ultrasound systems may include multiple probes, each using piezoelectric transducers tuned to different narrow portions of the broad frequency range. In contrast, the inventors have recognized that certain other types of ultrasonic transducers, such as capacitive micromachined ultrasonic transducers (CMUTs), may have broad bandwidths and therefore a single ultrasound device having a single transducer array of such transducers may enable imaging across a broad frequency range.

In short, certain aspects of the technology developed by the inventors include a single ultrasound device (which may be in the form factor of a probe, a patch, or some other form factor) based on broad bandwidth ultrasonic transducers and the ability to automatically configure the ultrasound device for detecting lung sliding or for detecting A lines and B lines based on user selection of imaging depth. However, it should be appreciated that the technology described herein is not limited to configuring an ultrasound device with imaging parameters optimized for imaging lung sliding, A lines, and B lines, but may generally include configuration of a single ultrasound device with different imaging parameters for different lung imaging modes based on selected imaging depth (where selection may be by the user or automatic). Furthermore, the technology described herein may generally include configuration of a single ultrasound device, based on selected imaging depth, with different imaging modes optimized for imaging other indications in lungs and other anatomical structures or regions.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

FIG. 1 illustrates an example process 100 for ultrasound imaging of lungs, in accordance with certain embodiments described herein. The process 100 is performed by a processing device in an ultrasound system. The processing device may be, for example, a mobile phone, tablet, or laptop in operative communication with an ultrasound device. The ultrasound device and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link).

For ultrasound imaging of the lungs, the processing device may configure the ultrasound device with a first lung imaging mode or a second lung imaging mode. For example, the first lung imaging mode may be a shallow lung imaging mode and the second lung imaging mode may be a deep lung imaging mode, each lung imaging mode associated with a different range of imaging depths and a different set of parameter values related to transmission of ultrasound pulses, reception of ultrasound pulses, and processing of ultrasound data. Further description of parameter values that may be used for the shallow lung imaging mode and the deep lung imaging mode may be found below. The shallow lung imaging mode may refer to a lung imaging mode used for imaging depths that are smaller than a threshold depth, and the deep lung imaging mode may refer to a lung imaging mode used for imaging depths that are greater than a threshold depth. Certain embodiments may use the shallow lung imaging mode for imaging depths that are equal to the threshold depth while other embodiments may use the deep lung imaging mode for imaging depths that are equal to the threshold depth. The shallow lung imaging mode may be optimized for imaging lung sliding and the deep lung imaging mode may be optimized for detecting A lines and B lines.

In act 102, the processing device configures the ultrasound device with a set of parameter values associated with a shallow lung imaging mode. To configure the ultrasound device with parameter values, the processing device may transmit configuration commands to the ultrasound device. In some embodiments, the shallow lung imaging mode may be the default lung imaging mode. As will be described further below, in some embodiments, act 102 may proceed in response to user selection of a lung imaging preset or in response to an automatic determination that lung imaging is being performed. Upon receiving the user selection of the lung imaging preset or the automatic determination that lung imaging is being performed, the processing device may be configured to configure the ultrasound device with parameter values corresponding to the default lung imaging mode (i.e., shallow lung imaging mode). When the processing device by default configures the ultrasound device with the set of parameter values associated with the shallow lung imaging mode, a default imaging depth may be used as one of the set of parameter values, and the default imaging depth may be less than the threshold imaging depth. In some embodiments, act 102 may proceed based on user selection of an imaging depth that is less than the threshold depth, as will described further below with reference to act 112. When act 102 proceeds based on user selection of an imaging depth, configuring the ultrasound device with the set of imaging parameters may include configuring the ultrasound device with the selected imaging depth. The process 100 proceeds from act 102 to act 104.

The ultrasound device may collect ultrasound data using the set of parameter values associated with the shallow lung imaging mode, with which the processing device configured the ultrasound device. The ultrasound device may transmit ultrasound pulses, receive ultrasound pulses, and/or process the ultrasound data in accordance with the set of parameter values associated with the shallow lung imaging mode. For example, the set of parameter values may define (among other parameters) transmit frequency, receive frequency, and image format. Further description of parameters and parameter values may be found below. In act 104, the processing device receives from the ultrasound device ultrasound data collected using the set of parameter values associated with the shallow lung imaging mode. For example, the processing device may receive raw acoustical data, scan lines generated from raw acoustical data, and/or one or more ultrasound images generated from raw acoustical data or scan lines from the ultrasound device. The processing device may continue to periodically receive ultrasound data from the ultrasound device during the process 100. For example, the processing device may receive ultrasound data collected using the set of parameter values associated with the shallow lung imaging mode one or more times before acts 106, 108, and/or 110. The process proceeds from act 104 to act 106.

The user may make a selection of a change in imaging depth using the processing device. For example, the user may select an imaging depth by swiping on a touch-enabled display of the processing device. In act 106, the processing device determines if a selection of a change in imaging depth has been received. For example, the processing device may determine if a swipe on the touch-enabled display has been received. Receiving a selection of a change in imaging depth may include receiving a selection of a particular imaging depth. The selected imaging depth may be different than the imaging depth that was previously selected. If a selection of a change in imaging depth has not been received, the process 100 repeats act 106, where the processing device continues to determine whether a selection of a changing in imaging depth have been received. On the other hand, if a selection of a change in imaging depth has been received, the process 100 proceeds to act 108. The processing device may perform the determination in act 106 periodically, and other operations of the processing device (e.g., receiving ultrasound data from the ultrasound device) may occur in between such determinations.

In act 108, the processing device compares the selected imaging depth to a threshold imaging depth. In some embodiments, the threshold imaging depth may determine whether the processing device configures the ultrasound device with the shallow lung imaging mode or with the deep lung imaging mode. When an imaging depth shallower than the threshold imaging depth is selected (either by the user or by default), the processing device may configure the ultrasound device with the shallow lung imaging mode. When an imaging depth deeper than the threshold imaging depth is selected (either by the user or by default), the processing device may configure the ultrasound device with the deep lung imaging mode. As described above, imaging lung sliding may require shallow imaging, while imaging A lines and B lines may require deep imaging. A user may control which lung imaging mode is selected, and which lung artifacts the ultrasound device is optimized for imaging, based on how the selected imaging depth compares to the threshold imaging depth. The threshold imaging depth may be selected such that shallower imaging depths are generally more appropriate for imaging lung sliding and deeper imaging depths are generally more appropriate for imaging A lines and B lines. The threshold imaging depth may be a parameter value with which the processing device configures the ultrasound device.

If the selected imaging depth is greater than the threshold imaging depth, the process 100 proceeds to act 110. If the selected imaging depth is less than or equal to the threshold imaging depth, the process 100 proceeds back to act 106, where the processing device continues to determine whether a selection of a change in imaging depth has been received. If the processing device determines at act 106 that the selected imaging depth is less than or equal to the threshold imaging depth, the processing device may configure the ultrasound device to use the selected imaging depth (not shown in FIG. 1), but not change the ultrasound device from using the shallow lung imaging mode. For example, if the previous imaging depth was 4 cm, the selected imaging depth is 5 cm, and the threshold imaging depth is 6 cm, the processing device may determine that 5 cm is less than 6 cm, configure the ultrasound device to use an imaging depth of 5 cm, but not change the ultrasound device from using the shallow lung imaging mode.

Act 110 occurs if the ultrasound device was previously using a shallow lung imaging mode and the processing device then determines in act 108 that the imaging depth selected in act 106 is greater than the threshold imaging depth. In act 110, the processing device configures the ultrasound device with a set of parameter values associated with the deep lung imaging mode. To configure the ultrasound device with parameter values, the processing device may transmit configuration commands to the ultrasound device. The process 100 proceeds from act 110 to act 112.

In act 112, the ultrasound device receives ultrasound data collected using the set of parameter values associated with the deep lung imaging mode. The processing device may continue to periodically receive ultrasound data from the ultrasound device during the process 100. For example, the processing device may receive ultrasound data collected using the set of parameter values associated with the deep lung imaging mode one or more times before acts 114, 116, and/or 102. Further description of act 112 may be found with reference to act 104. The process 100 proceeds from act 112 to act 114.

In act 114, the processing device determines if a selection of a change in imaging depth has been received. Further description of act 114 may be found with reference to act 106. If a selection of a change in imaging depth has not been received, the process 100 repeats act 114, where the processing device continues to determine whether a selection of a changing in imaging depth have been received. If a selection of a change in imaging depth has been received, the processing 100 proceeds to act 116.

In act 116, the processing device compares the selected imaging depth to the threshold imaging depth. If the selected imaging depth is less than or equal to the threshold imaging depth, the process 100 proceeds back to act 102, in which the processing device configures the ultrasound device with the set of parameter values associated with the shallow lung imaging mode. If the selected imaging depth is greater than the threshold imaging depth, the process 100 proceeds back to act 114, where the processing device continues to determine whether a selection of a change in imaging depth has been received. If the processing device determines at act 116 that the selected imaging depth is greater than the threshold imaging depth, the processing device may configure the ultrasound device to use the selected imaging depth (not shown in FIG. 1) but not change the ultrasound device from using the deep lung imaging mode. For example, if the previous imaging depth was 10 cm, the selected imaging depth is 9 cm, and the threshold imaging depth is 6 cm, the processing device may determine that 9 cm is greater than 6 cm, configure the ultrasound device to use an imaging depth of 9 cm, but not change the ultrasound device from using the deep lung imaging mode. In some embodiments, acts 112-116 may be absent. For example, the processing device may configure the ultrasound device with the deep lung imaging mode, but further ultrasound data may not be received, and the processing device may not check for further changes in imaging depth. In some embodiments, acts 104 and/or 112 may be absent. For example, the processing device may configure the ultrasound device, but not receive ultrasound data.

Figure 2:
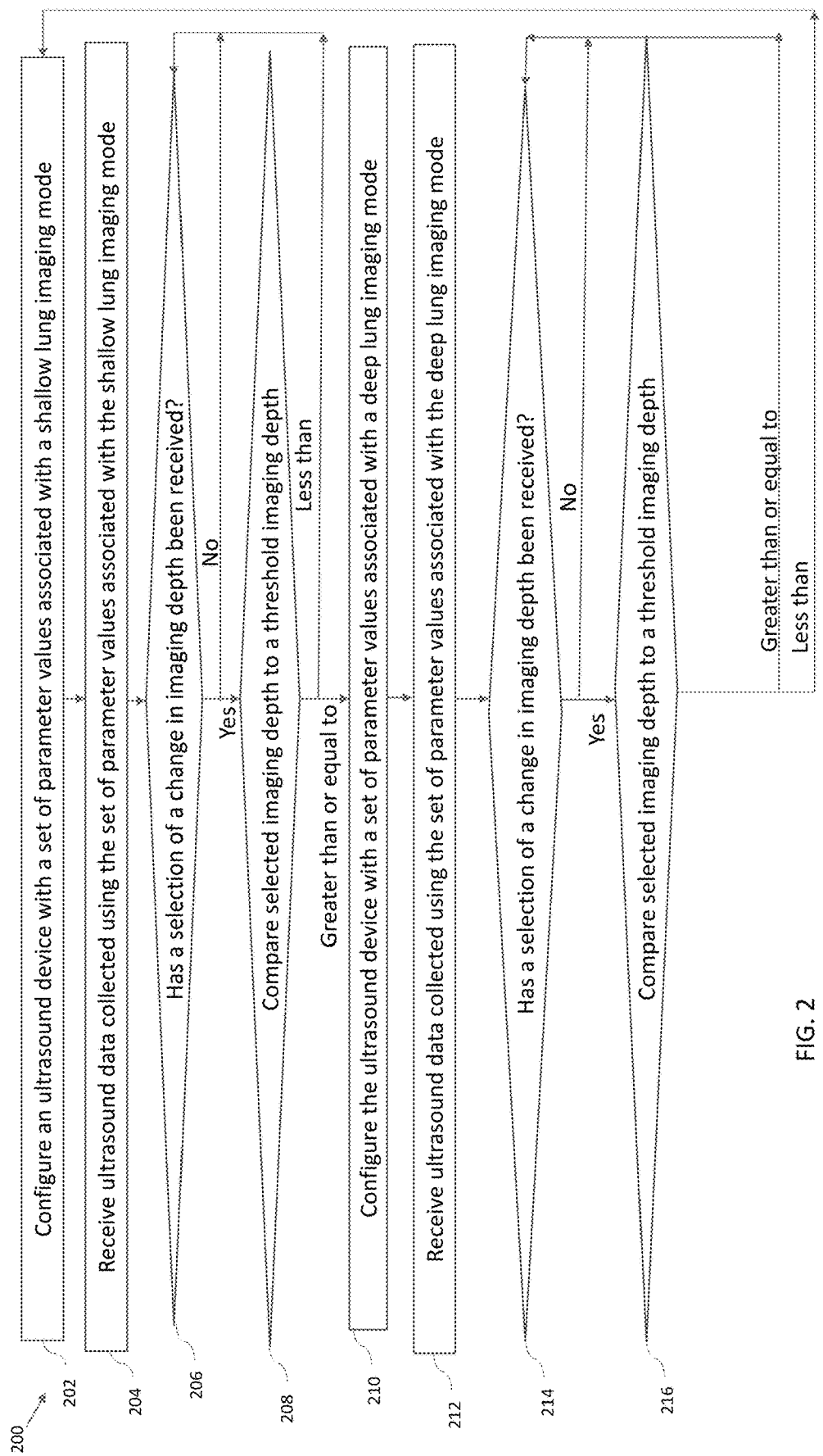
FIG. 2 illustrates an example process for ultrasound imaging of lungs, in accordance with certain embodiments described herein.

FIG. 2 illustrates another example process 200 for ultrasound imaging of lungs, in accordance with certain embodiments described herein. The process 200 may be performed by a processing device in an ultrasound system. In some embodiments, acts 202, 204, 206, 208, 210, 212, 214, and 216 may be the same as acts 102, 104, 106, 108, 110, 112, 114, and 116, respectively, with the following exceptions. The process 200 proceeds from act 208 to act 210 if the processing device determines at act 208 that the selected imaging depth is greater than or equal to the threshold imaging depth. The process 200 proceeds from act 208 to act 206 if the processing device determines at act 208 that the selected imaging depth is less than the threshold imaging depth. The process 200 proceeds from act 216 to act 214 if the processing device determines at act 216 that the selected imaging depth is greater than or equal to the threshold imaging depth. The process 200 proceeds from act 216 to act 202 if the processing device determines at act 216 that the selected imaging depth is less than the threshold imaging depth. In some embodiments, acts 212-216 may be absent. For example, the processing device may configure the ultrasound device with the deep lung imaging mode, but further ultrasound data may not be received, and the processing device may not check for further changes in imaging depth. In some embodiments, acts 204 and/or 212 may be absent. For example, the processing device may configure the ultrasound device, but not receive ultrasound data. Any aspects of the process 100 may apply to the process 200 as well.

Figure 3:
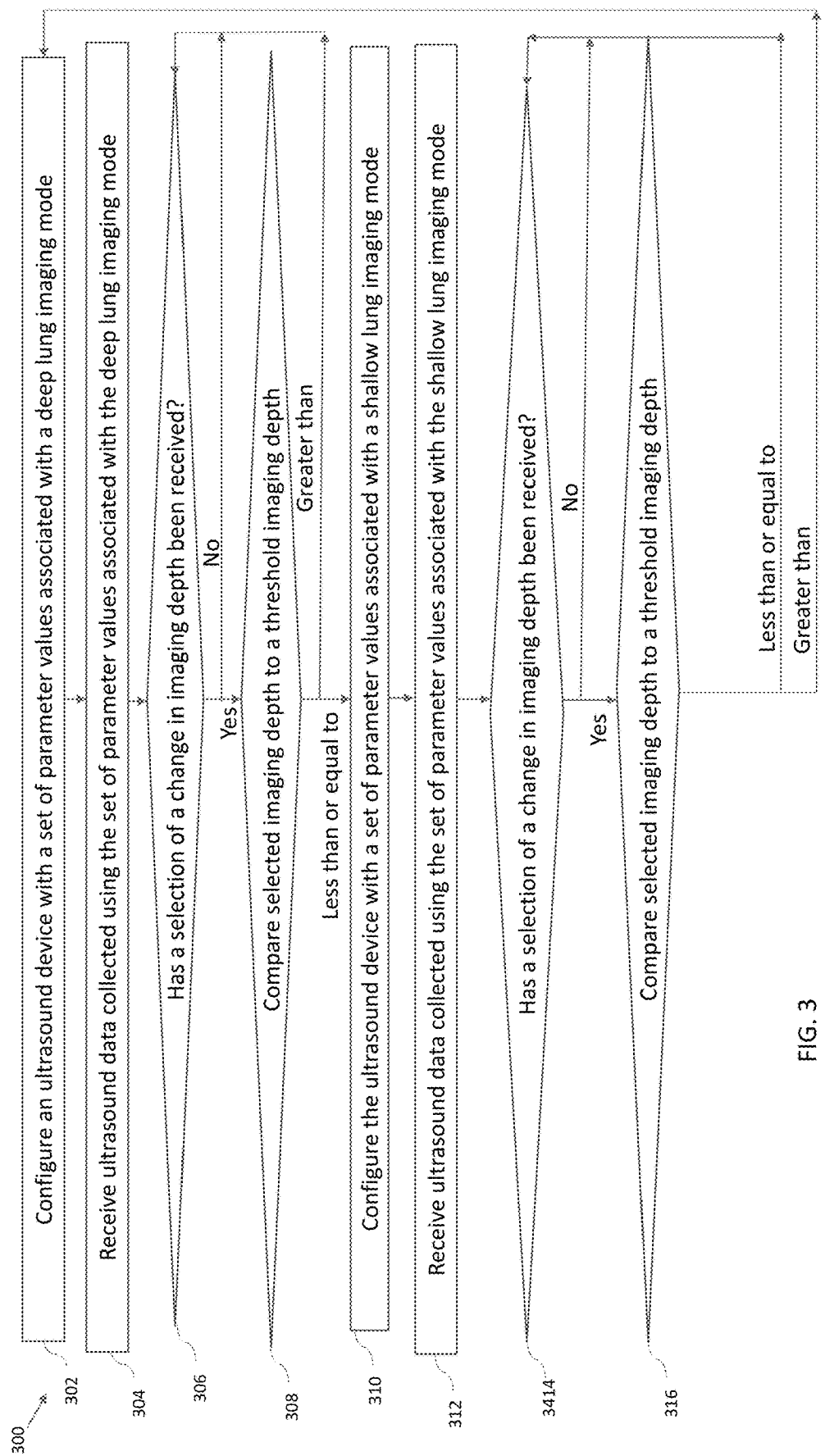
FIG. 3 illustrates another example process for ultrasound imaging of lungs, in accordance with certain embodiments described herein.

FIG. 3 illustrates another example process 300 for ultrasound imaging of lungs, in accordance with certain embodiments described herein. The process 300 may be performed by a processing device in an ultrasound system. In some embodiments, acts 302, 304, 306, 308, 310, 312, 314, and 316 may be the same as acts 102, 104, 106, 108, 110, 112, 114, and 116, respectively, with the following exceptions. At act 302, the processing device configures the ultrasound device with the set of parameter values associated with the deep lung imaging mode. Thus, the deep lung imaging mode may be the default lung imaging mode. At act 304, the processing device receives ultrasound data collected using the set of parameter values associated with the deep lung imaging mode. At act 310, the processing device configures the ultrasound device with the set of parameter values associated with the shallow lung imaging mode. At act 312, the processing device receives ultrasound data collected using the set of parameter values associated with the shallow lung imaging mode. The process 300 proceeds from act 308 to act 306 if the processing device determines at act 208 that the selected imaging depth is greater than the threshold imaging depth, and the process 300 proceeds from act 308 to act 310 if the processing device determines at act 308 that the selected imaging depth is less than or equal to the threshold imaging depth. Additionally, the process 300 proceeds from act 316 to act 314 if the processing device determines at act 316 that the selected imaging depth is less than or equal to the threshold imaging depth, and the process 300 proceeds from act 316 to act 302 if the processing device determines at act 316 that the selected imaging depth is greater than the threshold imaging depth. In some embodiments, acts 312-316 may be absent. For example, the processing device may configure the ultrasound device with the shallow lung imaging mode, but further ultrasound data may not be received, and the processing device may not check for further changes in imaging depth. In some embodiments, acts 304 and/or 312 may be absent. For example, the processing device may configure the ultrasound device, but not receive ultrasound data. Any aspects of the process 100 may apply to the process 300 as well.

Figure 4:
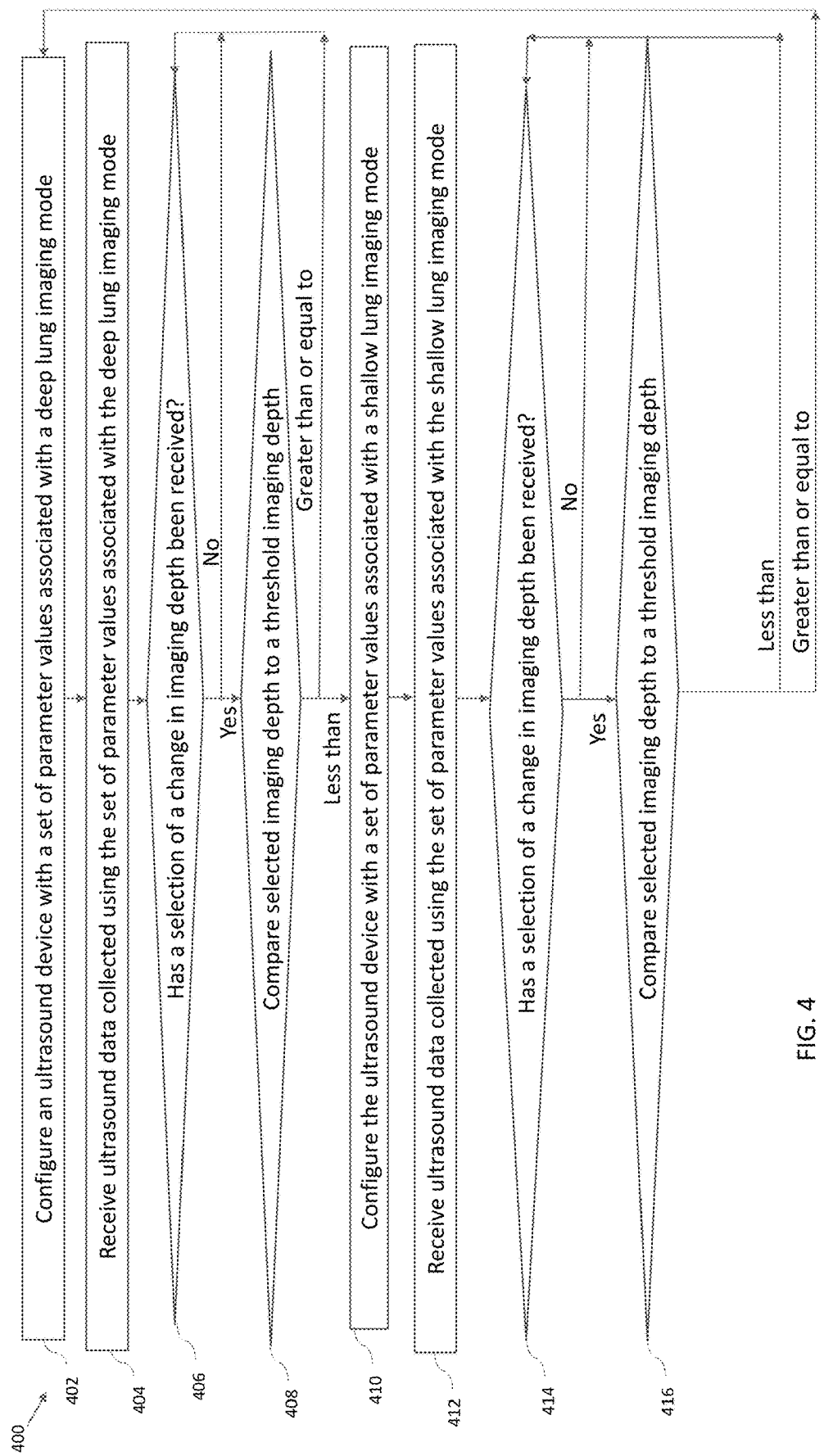
FIG. 4 illustrates an example process for ultrasound imaging of lungs, in accordance with certain embodiments described herein.

FIG. 4 illustrates another example process 400 for ultrasound imaging of lungs, in accordance with certain embodiments described herein. The process 400 may be performed by a processing device in an ultrasound system. In some embodiments, acts 402, 404, 406, 408, 410, 412, 414, and 416 may be the same as acts 302, 304, 306, 308, 310, 312, 314, and 316, respectively, with the following exceptions. The process 400 proceeds from act 408 to act 410 if the processing device determines at act 408 that the selected imaging depth is less than the threshold imaging depth. The process 400 proceeds from act 408 to act 406 if the processing device determines at act 408 that the selected imaging depth is greater than or equal to the threshold imaging depth. The process 400 proceeds from act 416 to act 414 if the processing device determines at act 416 that the selected imaging depth is less than the threshold imaging depth. The process 400 proceeds from act 416 to act 402 if the processing device determines at act 416 that the selected imaging depth is greater than or equal to the threshold imaging depth. In some embodiments, acts 412-416 may be absent. For example, the processing device may configure the ultrasound device with the shallow lung imaging mode, but further ultrasound data may not be received, and the processing device may not check for further changes in imaging depth. In some embodiments, acts 404 and/or 412 may be absent. For example, the processing device may configure the ultrasound device, but not receive ultrasound data. Any aspects of the process 300 may apply to the process 400 as well.

In some embodiments, the processes 100, 200, 300, and 400 may include receiving a selection of lung imaging. For example, the processes 100, 200, 300, and 400 may only proceed with acts 102, 202, 302, and 402, respectively, responsive to receiving the selection of lung imaging. In some embodiments, the processing device may receive the selection of lung imaging from a user, who may select a lung imaging preset option from a menu of preset options. In some embodiments, the processes 100, 200, 300, and 400 may include automatically determining that lung imaging is being performed. For example, the processes 100, 200, 300, and 400 may only proceed with acts 102, 202, 302, and 402, respectively, in response to an automatic determination that lung imaging is being performed. For example, the processing device may receive ultrasound data from the ultrasound device and determine that the ultrasound data was collected from the lungs based on the ultrasound data. The ultrasound data may include, for example, raw acoustical data, scan lines generated from raw acoustical data, or one or more ultrasound images generated from raw acoustical data. In some embodiments, the ultrasound device may generate scan lines and/or ultrasound images from raw acoustical data and transmit the scan lines and/or ultrasound images to the processing device. In some embodiments, the ultrasound device may transmit the raw acoustical data to the processing device and the processing device may generate the scan lines and/or ultrasound images from the raw acoustical data. In some embodiments, the ultrasound device may generate scan lines from the raw acoustical data, transmit the scan lines to the processing device, and the processing device may generate ultrasound images from the scan lines. Any form of ultrasound data may be used to determine that lung imaging is being performed. To determine that the ultrasound data was collected from the lungs, the processing device may input the ultrasound data to a statistical model. The statistical model may be trained to accept ultrasound data as an input and determine the anatomical region on the subject where the ultrasound data was collected. To train the statistical model, ultrasound data labeled with the anatomical region on the subject where the ultrasound data was collected may be inputted to the statistical model and used to modulate internal parameters of the statistical model.

As another example, the processing device may receive an optical image of the ultrasound device and the subject and determine that the ultrasound device is located at the subject's lungs. In some embodiments, the processing device may capture the optical image of the ultrasound device and the subject with a camera on the processing device. For example, a user may hold the hold the ultrasound device on the subject with one hand and hold the processing device in another hand such that the subject and the ultrasound device are in view of the camera of the processing device. To determine that the ultrasound device is located at the subject's lungs, the processing device may input the ultrasound data to a statistical model. The statistical model may be trained to accept an optical image of an ultrasound device on a subject as an input and determine the anatomical region on the subject where the ultrasound device is located. To train the statistical model, optical images of ultrasound devices on subjects labeled with the anatomical region where the ultrasound device is located may be inputted to the statistical model and used to modulate internal parameters of the statistical model. In some embodiments, the processing device may be configured for lung imaging by default, and no selection or automatic determination of lung imaging may be necessary for the processes 100, 200, 300, and 400 to proceed with acts 102, 202, 302, and 402, respectively.

Some embodiments may be the same as the processes 100, 200, 300, and 400, but instead of the shallow lung imaging mode and the deep lung imaging mode, the imaging modes may be a first imaging mode and a second imaging mode for imaging other anatomical structures or regions. The first and second imaging modes may be optimized for detecting other indications besides lung sliding, A lines, and B lines.

While the above description has described the processes 100, 200, 300, and 400 as being performed by a processing device in operative communication with an ultrasound device, in some embodiments the processes 100, 200, 300, and 400 may be performed by the ultrasound device itself. Thus, the ultrasound device may configure itself with sets of parameter values, receive ultrasound data, determine if a selection of a change in imaging depth has been received, compare the selected imaging depth to a threshold imaging depth, etc. In some embodiments, portions of the processes 100, 200, 300, and 400 may be performed by the processing device and other portions may be performed by the ultrasound device.

The following description will describe example imaging parameter values that may be used in a shallow lung imaging mode and imaging parameter values that may be used in a deep lung imaging mode. In general, generation of an ultrasound image proceeds as follows. Ultrasound pulses are transmitted into a subject and reflected back at various tissue interfaces. The received analog ultrasound pulses are converted into digitized ultrasound data. The digitized ultrasound data is processed into scan lines, each of which is a collection of ultrasound reflections received from locations along a single direction. Scan lines are then converted into an ultrasound image having an array of pixels, each pixel having one or more values determining how the pixel appears relative to other pixels in the image. Imaging parameters values may relate to any of these steps.

The shallow lung imaging mode may be optimized for detecting lung sliding while the deep lung imaging mode may be optimized for detecting A lines and B lines. As described above, in some embodiments, configuring an ultrasound device with the shallow lung imaging mode may be responsive to determining that a selected imaging depth is smaller than a threshold imaging depth. Configuring the ultrasound device with the deep lung imaging mode may be responsive to determining that a selected imaging depth is larger than a threshold imaging depth. In some embodiments, the threshold imaging depth may be between approximately 4 cm and 8 cm (e.g., 4 cm, 5 cm, 6 cm, 7 cm, or 8 cm, or any other value within that range), although other ranges are possible. The threshold imaging depth may be related to the typical pleural depth in order to place the pleura approximately in the middle of an ultrasound image collected in the shallow imaging mode. For example, if a typical pleural depth of 3 cm is assumed, the threshold imaging depth may be selected to be 6 cm such that in the shallow lung imaging mode, at an imaging depth of 6 cm, the pleura may be in the middle of collected ultrasound images.

In some embodiments, in shallow lung imaging mode, the peak frequency of transmitted ultrasound (i.e., the peak frequency of the frequency spectrum of transmitted ultrasound energy) may be between approximately 5 MHz and 10 MHz (e.g., 5 MHz, 6 MHz, 7 MHz, 8 MHz, 9 MHz, 10 MHz, or any other value within that range). In some embodiments, in deep lung imaging mode, the peak frequency of transmitted ultrasound may be between approximately 2 MHz and 5 MHz (e.g., 2 MHz, 3 MHz, 4 MHz, 5 MHz, or any other value within that range). In some embodiments, in either or both of shallow lung imaging mode and deep lung imaging mode, the full-width-at-half-maximum bandwidth may be between approximately 1 MHz and 4 MHz (e.g., 1 MHz, 2 MHz, 3 MHz, 4 MHz, or any other value within that range). As described above, high ultrasound transmit frequency may be appropriate for detecting lung sliding while low ultrasound transmit frequency may be appropriate for detecting A lines and B lines. In some embodiments, in shallow lung imaging mode, the receive frequency, namely the received ultrasound frequency used for image reconstruction, may be between approximately 5 MHz and 10 MHz (e.g., 5 MHz, 6 MHz, 6.25 MHz, 7 MHz, 8 MHz, 9 MHz, 10 MHz, or any other value within that range). In some embodiments, in deep lung imaging mode, the receive frequency may between approximately 2 MHz and 5 MHz (e.g., 2 MHz, 3 MHz, 4 MHz, 5 MHz, or any other value within that range).

An ultrasound device may transmit ultrasound pulses towards a set of focal points, and receive ultrasound pulses along a set of scan lines. These focal points may lie on a circle centered at a spatial point above the skin line known as the virtual apex. The angular extent of these focal points around the virtual apex is known as the image field of view (FOV) angle. Each transmitted pulse may be generated by a sub-set of the transducer array centered on the intersection of the line between the focal point and the virtual apex, except where this intersection falls beyond the transducer array, in which case the nearest sub-set of the transducer array is used. The width of the sub-set of the transducer array used for each transmitted pulse is known as the instantaneous transmit aperture (measured along the long axis of the transducer array). The scan lines may lie along a set of directions intersecting at the virtual apex. In some embodiments, in shallow lung imaging mode, the virtual apex may be greater than or equal to approximately 10 cm above the skin line. In some embodiments, in shallow lung imaging mode, the image field of view (FOV) angle may be between approximately 0 degrees and 20 degrees (e.g., 0 degrees, 5 degrees, 10 degrees, 15 degrees, 20 degrees, or any other value within that range) around the virtual apex. In some embodiments, in shallow lung imaging mode, the instantaneous transmit aperture may be between approximately 4 mm and 8 mm (e.g., 4 mm, 5 mm, 6 mm, 7 mm, 8 mm, or any other value within that range). Because the transmit directions of ultrasound pulses may follow radial paths from the virtual apex, with a large virtual apex and a small image FOV angle, most of the transmits may be roughly perpendicular to the face of the ultrasound device. Thus, the ultrasound device may insonify an approximately rectangular-shaped region under the transducer array, and resulting ultrasound images may have a linear image format (i.e., a rectangular shape). Insonifying an approximately rectangular-shaped region under the transducer array may be helpful in the shallow lung imaging mode because such a shape, contrasted with other shapes such as wedge shapes, may result in larger imaging areas at shallow depths.

In some embodiments, in deep lung imaging mode, the virtual apex may be between approximately 0 cm and 5 cm (e.g., 0 cm, 1 cm, 1.3 cm, 2 cm, 3 cm, 4 cm, 5 cm, or any other value within that range) above the skin line. In some embodiments, in deep lung imaging mode, the image FOV angle may be between approximately 40 degrees and 90 degrees (e.g., 40 degrees, 50 degrees, 60 degrees, 70 degrees, 80 degrees, 90 degrees, or any other value within that range). In some embodiments, in deep lung imaging mode, the instantaneous transmit aperture may be approximately 12 mm and 30 mm (e.g., 12 mm, 17 mm, 22 mm, 27 mm, 30 mm, or any other value within that range). With a small virtual apex and a large image FOV angle, the ultrasound device may insonify an approximately wedge-shaped region under the aperture, and resulting ultrasound images may have a sector image format (i.e., a wedge shape). Insonifying an approximately wedge-shaped region may help to image a wider area in the deep lung imaging mode by transmitting ultrasound pulses over a range of directions. Ultrasound pulses transmitted over a range of directions may diverge at large depths and result in the wedge-shaped imaging region. In either mode, the instantaneous transmit aperture may be dependent on the virtual apex and the image FOV angle.

In some embodiments, different gains may be applied to digitized ultrasound signals received from different depth ranges to account for varying tissue properties as a function of depth. This may be referred to as time-gain compensation (TGC). In some embodiments, the TGC may be a piecewise linear function described by a set of control points (depths) and a set of gain values (dB), one gain value at each control point. The value of the piecewise linear function at a given depth may be the gain applied to the ultrasound signals received from that given depth. For depths outside the specified range of control points, the TGC may be equal to the gain at the nearest control point. In shallow lung imaging mode, the TGC gain values may be approximately 0 dB, −8 dB, and −2 dB, at respective control points that are approximately 0 cm, 3 cm, and 6 cm. The reduced gain around the 3-cm control point may help to keep the pleural line from saturating in ultrasound images, and thereby help enable visualization of the shimmering effect, which is characteristic of lung sliding, in ultrasound images. In some embodiments, in deep lung imaging mode, the TGC gains may be approximately 0 dB, 0 dB, and 5 dB at respective control points that are approximately 0 cm, 3 cm, and 6 cm, respectively. Increasing the gain at depths larger than approximately 3 cm may help to reconstruct A line artifacts.

Table 1 summarizes the various example parameter values for the shallow lung imaging mode and the deep lung imaging mode described above:

TABLE 1

Summary of example parameter values for the shallow lung imaging mode and the deep lung imaging mode.

| Parameter | Shallow Lung Imaging Mode Parameter Value | Deep Lung Imaging Mode Parameter Value |
|---|---|---|
| Peak Frequency of Transmitted Ultrasound | 5 MHz-10 MHz | 2 MHz-5 MHz |
| Receive Frequency | 5 MHz-10 MHz | 2 MHz-5 MHz |
| Virtual Apex | ≥10 cm above skin line | 0 cm-5 cm above skin line |
| Image Field of View Angle Around Virtual Apex | ≤20 degrees | 40 degrees-90 degrees |
| Instantaneous Transmit Aperture | 4 mm-8 mm | 12 mm-20 mm |
| Image Format | Linear | Sector |
| Time-Gain Compensation Gain Values and Control Points | 0 dB at 0 cm −8 dB at 3 cm −2 dB at 6 cm | 0 dB at 0 cm 0 dB at 3 cm 5 dB at 6 cm |

Figure 5:
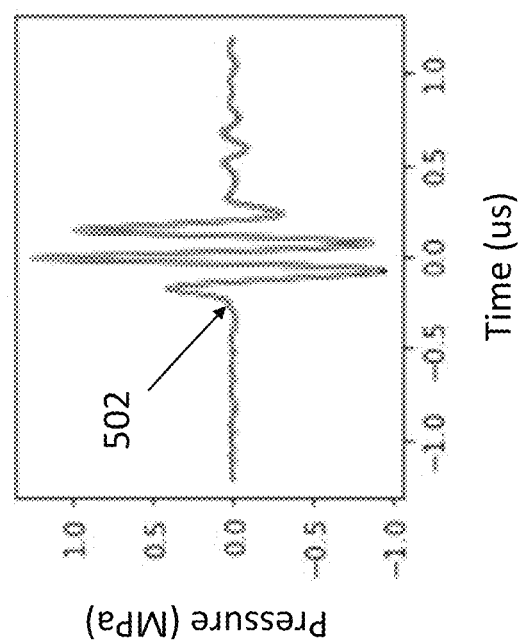
FIG. 5 illustrates an example graph of a transmitted ultrasound pulse profile in a shallow lung imaging mode, in accordance with certain embodiments described herein.

FIG. 5 illustrates an example graph of a transmitted ultrasound pulse profile 502 in a shallow lung imaging mode, in accordance with certain embodiments described herein. The graph of FIG. 5 illustrates pulse pressure as a function of time.

Figure 6:
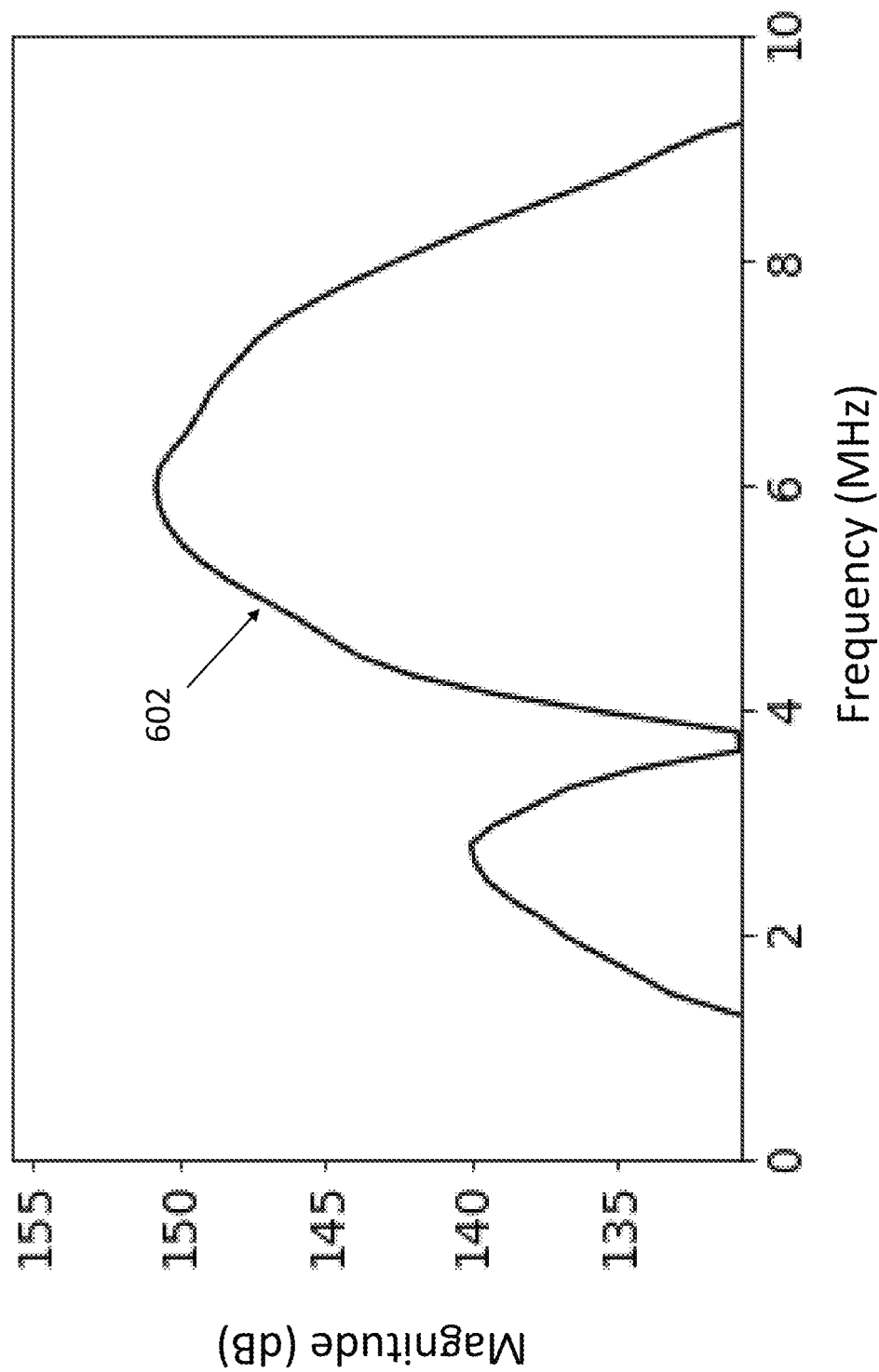
FIG. 6 illustrates an example graph of a frequency spectrum of a transmitted ultrasound pulse in a shallow lung imaging mode, in accordance with certain embodiments described herein.

FIG. 6 illustrates an example graph of a frequency spectrum 602 of a transmitted ultrasound pulse in a shallow lung imaging mode, in accordance with certain embodiments described herein. The graph of FIG. 6 illustrates the magnitude of frequency components of the ultrasound pulse illustrated in FIG. 5. A peak frequency of approximately 6 MHz is visible in the graph.

Figure 7:
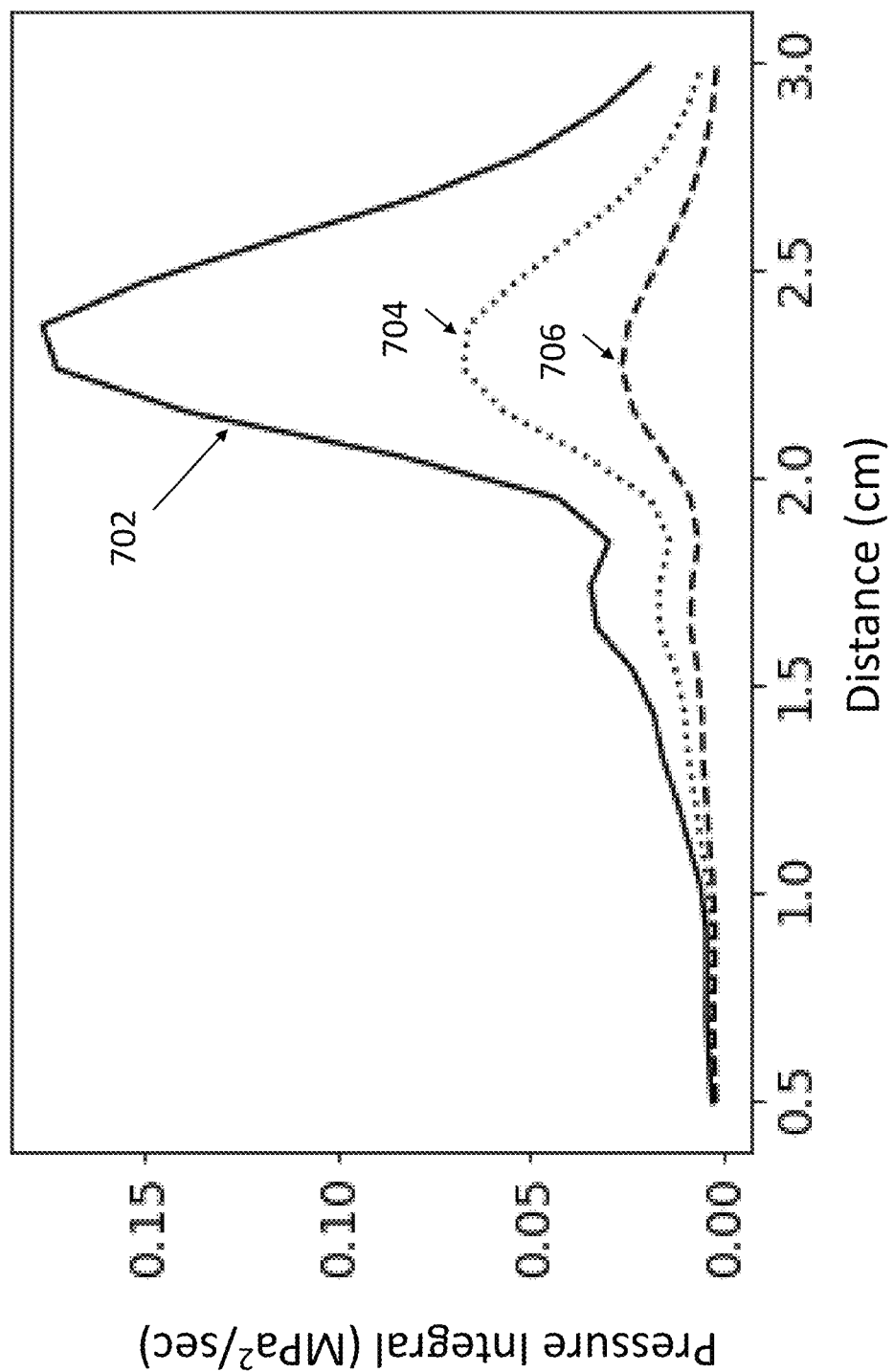
FIG. 7 illustrates an example graph of an axial scan of a transmitted ultrasound beam in a shallow lung imaging mode, in accordance with certain embodiments described herein.

FIG. 7 illustrates an example graph of an axial scan of a transmitted ultrasound beam in a shallow lung imaging mode, in accordance with certain embodiments described herein. FIG. 7 illustrates measurements of ultrasound power (more particularly, pulse pressure integral) as a function of distance directly down boresight of the ultrasound transducer array. Three plots are shown in the graph in FIG. 7. One plot 702 is a measurement in a water tank, one plot 704 includes a typical soft tissue attenuation (−0.3 dB/MHz/cm) applied to the water tank measurement, and one plot 706 includes a typical bone attenuation (−0.6 dB/MHz/cm) applied to the water tank measurement. The depth where the axial scan plot peaks may be considered the transmit focus. In FIG. 7, the transmit focus is at approximately 2.25 cm.

Figure 8:
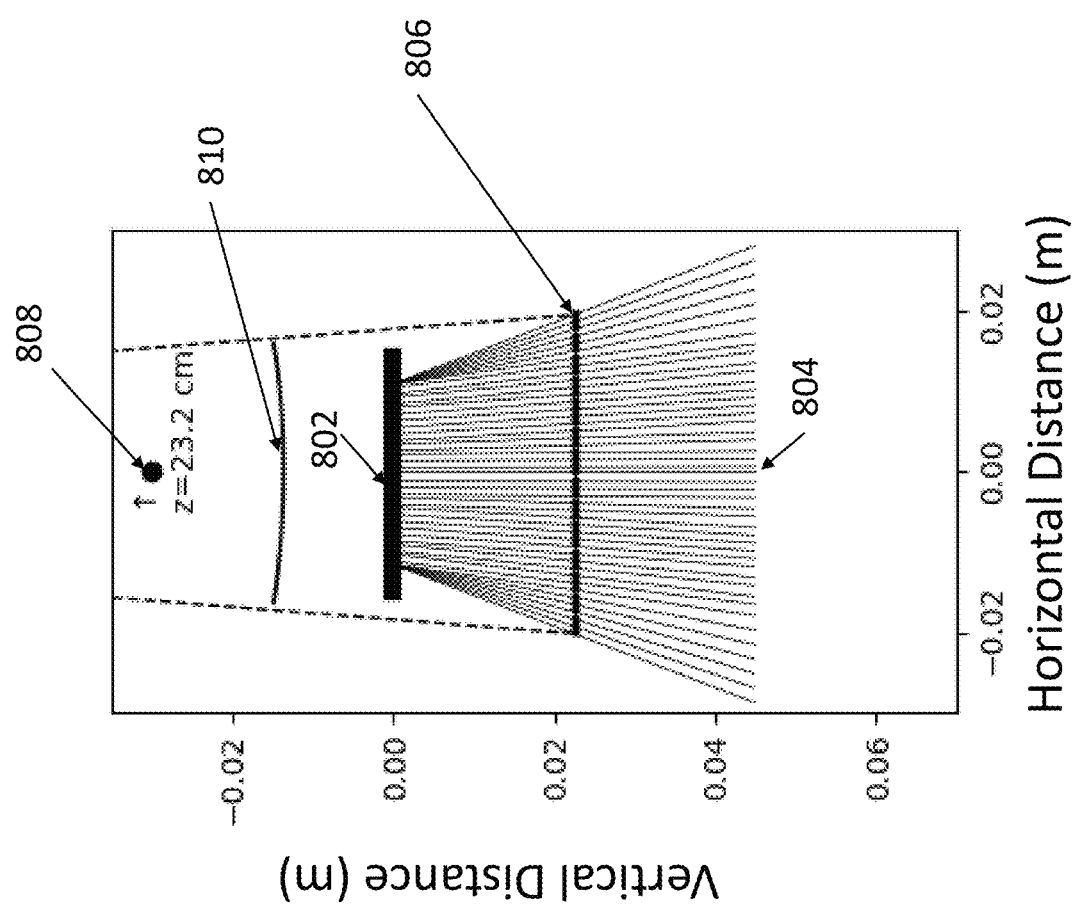
FIG. 8 illustrates an example graph of the locations of a transducer array, ultrasound transmit lines, transmit focal points, virtual apex, and field-of-view (FOV) angle during a transmit event in a shallow lung imaging mode, in accordance with certain embodiments described herein.

FIG. 8 illustrates an example graph of the locations of the transducer array 802, ultrasound transmit lines 804, transmit focal points 806, virtual apex 808, and FOV angle 810 during a transmit event in a shallow lung imaging mode, in accordance with certain embodiments described herein. The ultrasound transmit lines 804 are shown as terminating at twice the depth of the transmit focal points 806. The approximately rectangular shape of the insonified region is visible in FIG. 8. The virtual apex 808 is not shown at its actual location; FIG. 8 indicates that the virtual apex 808 is located beyond the limits of the graph in FIG. 8, at 23.2 cm.

Figure 9:
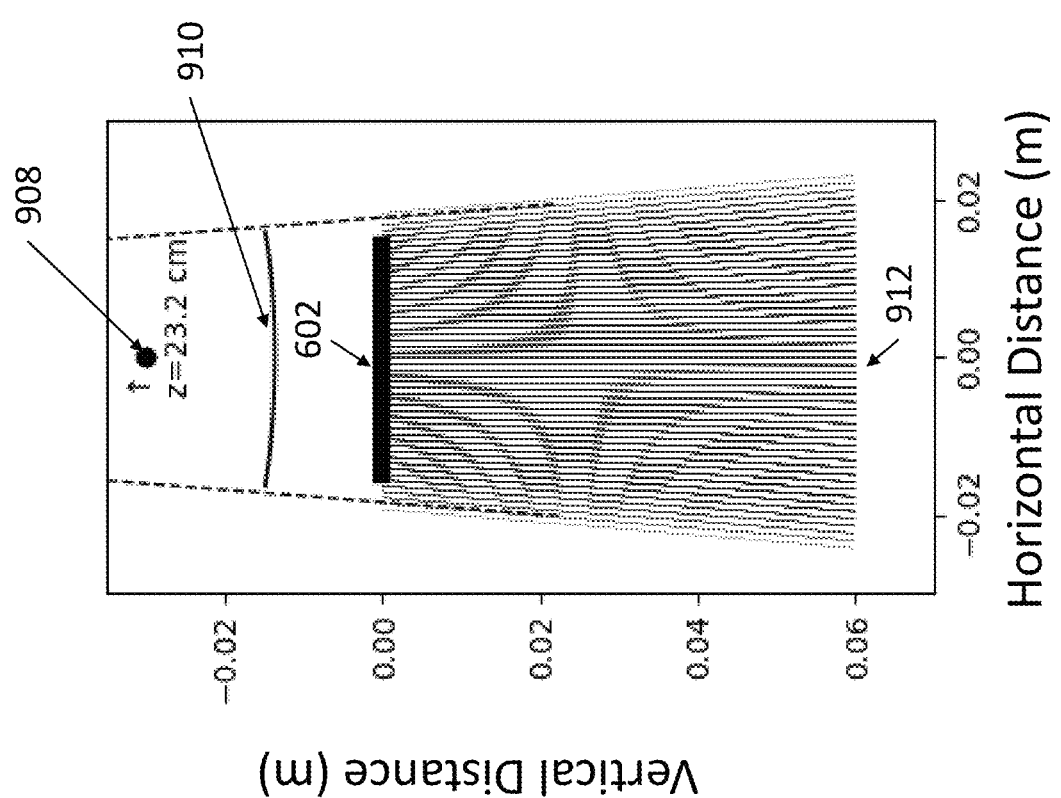
FIG. 9 illustrates an example graph of the locations of a transducer array, ultrasound scan lines, virtual apex, and FOV angle during a receive event in a shallow lung imaging mode, in accordance with certain embodiments described herein.

FIG. 9 illustrates an example graph of the locations of the transducer array 602, ultrasound scan lines 912, virtual apex 908, and the FOV angle 910 during a receive event in a shallow lung imaging mode, in accordance with certain embodiments described herein. For clarity, every other scan line 912 is illustrated in FIG. 9.

Figure 10:
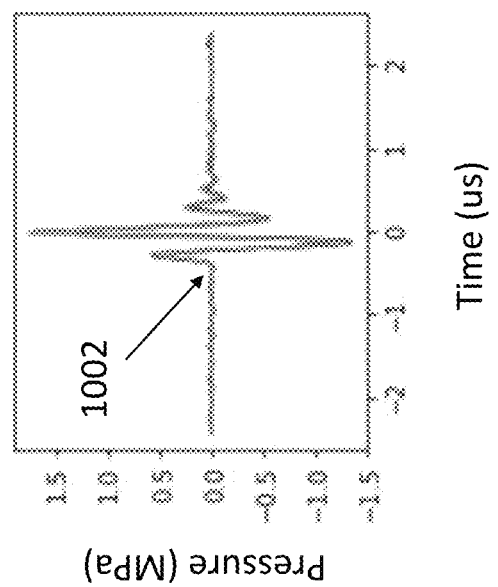
FIG. 10 illustrates an example graph of a transmitted ultrasound pulse profile in a deep lung imaging mode, in accordance with certain embodiments described herein.

FIG. 10 illustrates an example graph of a transmitted ultrasound pulse profile 1002 in a deep lung imaging mode, in accordance with certain embodiments described herein. The graph of FIG. 10 is the deep lung imaging mode equivalent of FIG. 5.

Figure 11:
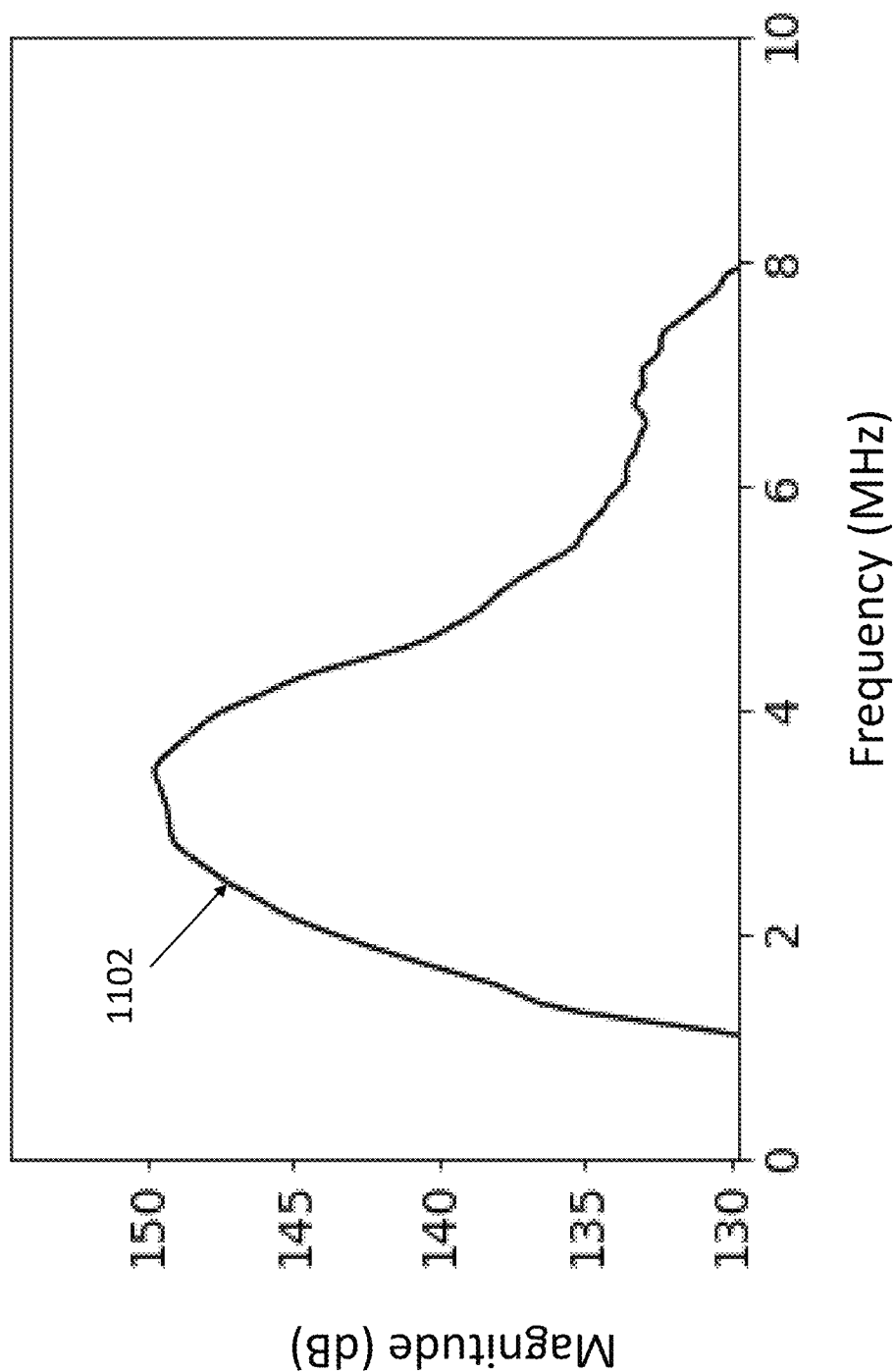
FIG. 11 illustrates an example graph of a frequency spectrum of a transmitted ultrasound pulse in a deep lung imaging mode, in accordance with certain embodiments described herein.

FIG. 11 illustrates an example graph of a frequency spectrum 1102 of a transmitted ultrasound beam in a deep lung imaging mode, in accordance with certain embodiments described herein. The graph of FIG. 11 is the deep lung imaging mode equivalent of FIG. 6.

Figure 12:
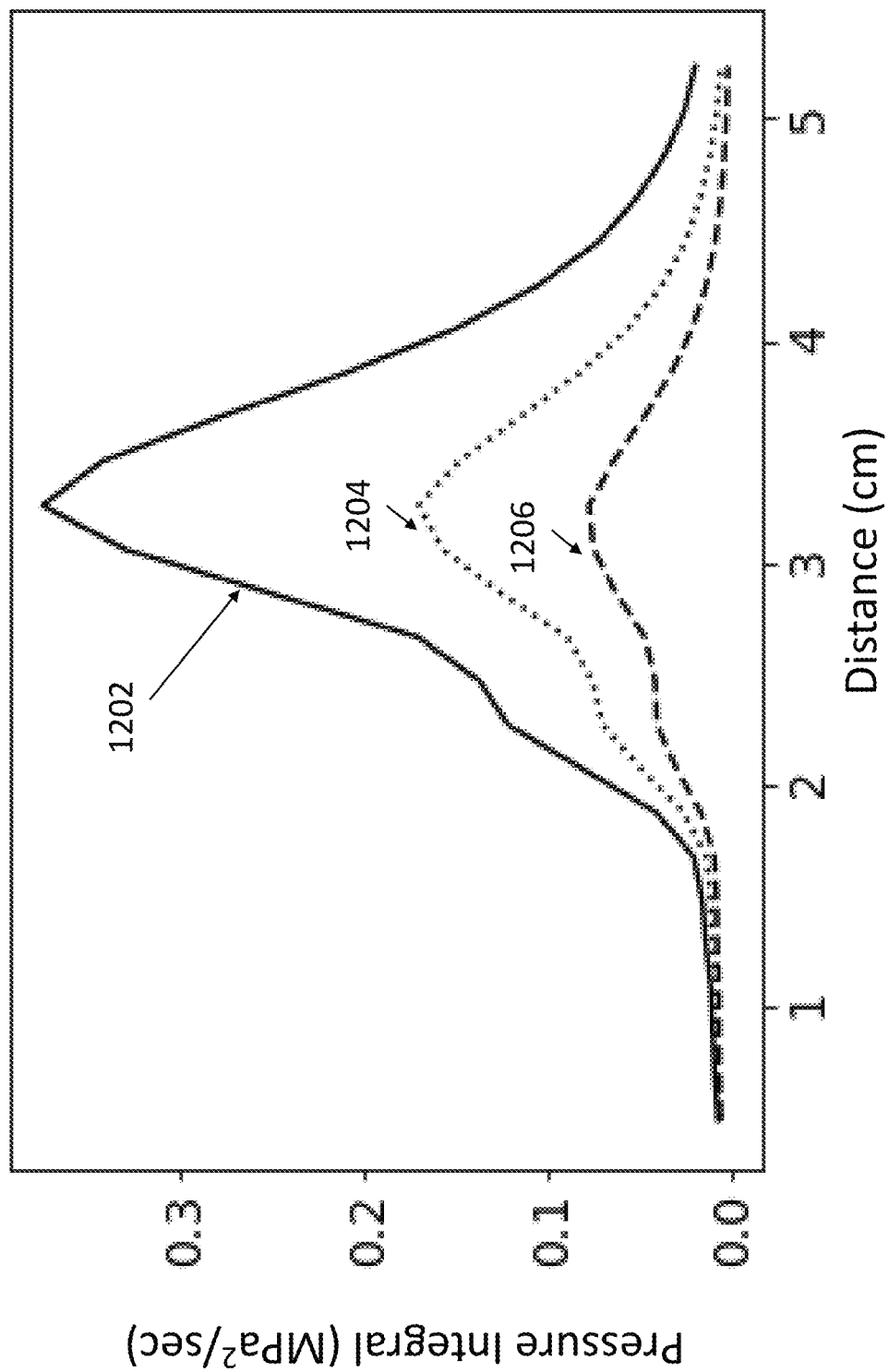
FIG. 12 illustrates an example graph of an axial scan of a transmitted ultrasound beam in a deep lung imaging mode, in accordance with certain embodiments described herein.

FIG. 12 illustrates an example graph of an axial scan of an ultrasound pulse in a deep lung imaging mode, in accordance with certain embodiments described herein. FIG. 12 is the deep lung imaging mode equivalent of FIG. 7. One plot 1202 is a measurement in a water tank, one plot 1204 includes the typical soft tissue attenuation, and one plot 1206 includes the typical bone attenuation. In FIG. 12, the transmit focus is at approximately 3.25 cm.

Figure 13:
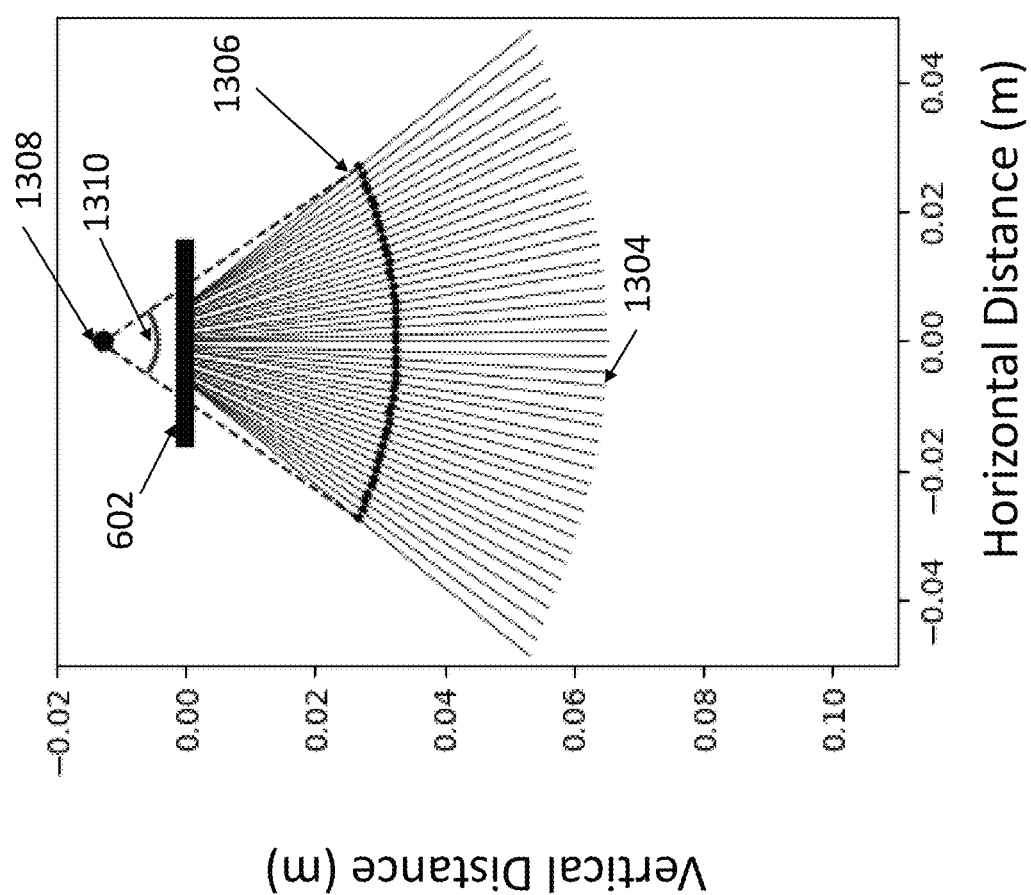
FIG. 13 illustrates an example graph of the locations of a transducer array, ultrasound transmit lines, transmit focal points, virtual apex, and FOV angle during a transmit event in a deep lung imaging mode, in accordance with certain embodiments described herein.

FIG. 13 illustrates an example graph of the locations of the transducer array 602, ultrasound transmit lines 1304, transmit focal points 1306, virtual apex 1308, and FOV angle 1310 during a transmit event in a deep lung imaging mode, in accordance with certain embodiments described herein. FIG. 13 is the deep lung imaging mode equivalent of FIG. 8. The approximately wedge shape of the insonified region is visible in FIG. 13. The virtual apex 1308 is shown at its actual location.

Figure 14:
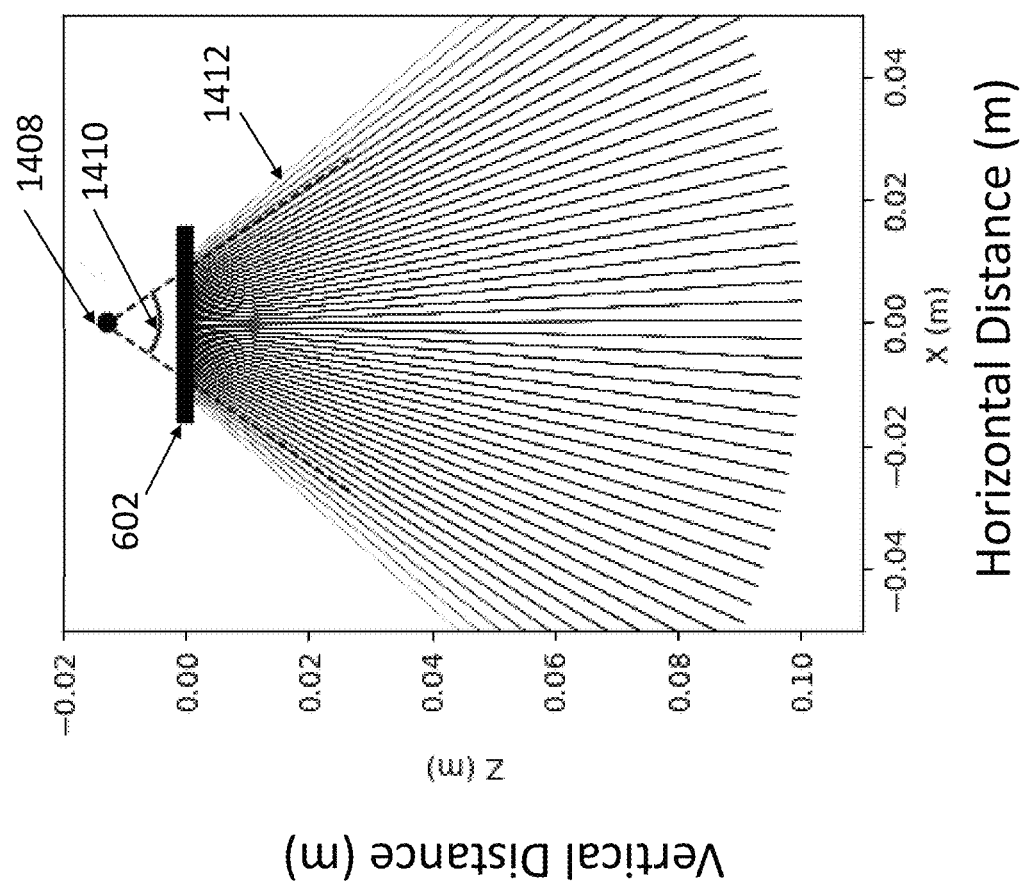
FIG. 14 illustrates an example graph of the locations of a transducer array, ultrasound scan lines, virtual apex, and FOV angle during a receive event in a deep lung imaging mode, in accordance with certain embodiments described herein.

FIG. 14 illustrates an example graph of the locations of the transducer array 602, ultrasound scan lines 1412, virtual apex 1408, and FOV angle 1410 during a receive event in a deep lung imaging mode, in accordance with certain embodiments described herein. FIG. 14 is the deep lung imaging mode equivalent of FIG. 9.

Figure 15:
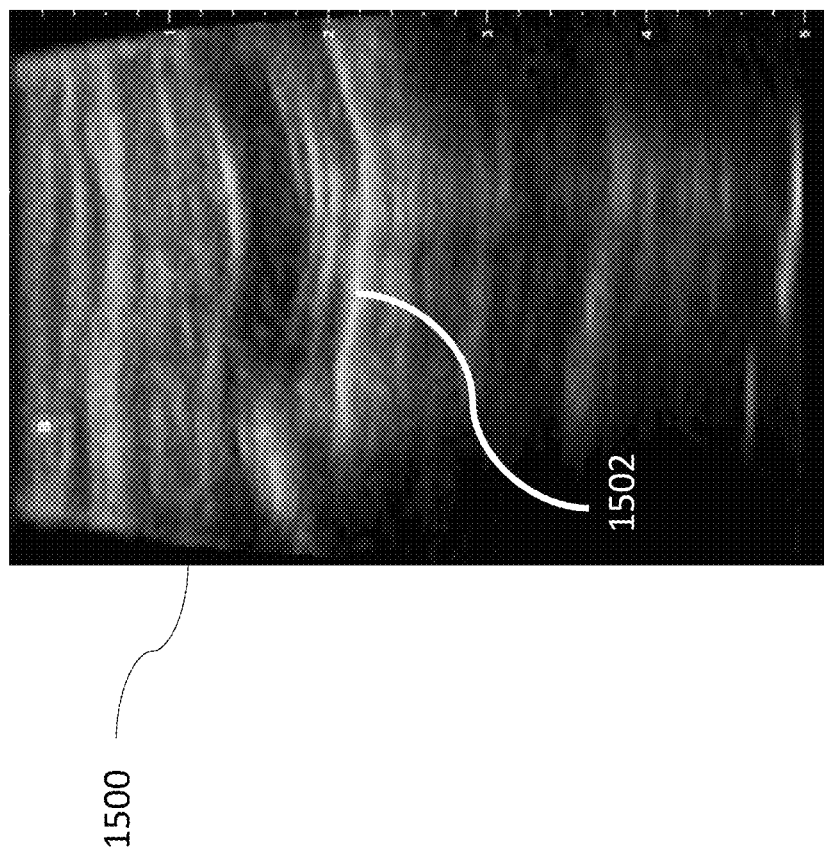
FIG. 15 illustrates an ultrasound image of the lungs collected using an ultrasound probe and a shallow lung imaging mode, in accordance with certain embodiments described herein.

FIG. 15 illustrates an ultrasound image 1500 of the lungs collected using an ultrasound device and a shallow lung imaging mode, in accordance with certain embodiments described herein. The ultrasound image 1500 was collected using an imaging depth of 5 cm. The pleura 1502 are visible in the ultrasound image 1502 in sufficient detail such that in a sequence of such ultrasound images, lung sliding is visible.

Figure 16:
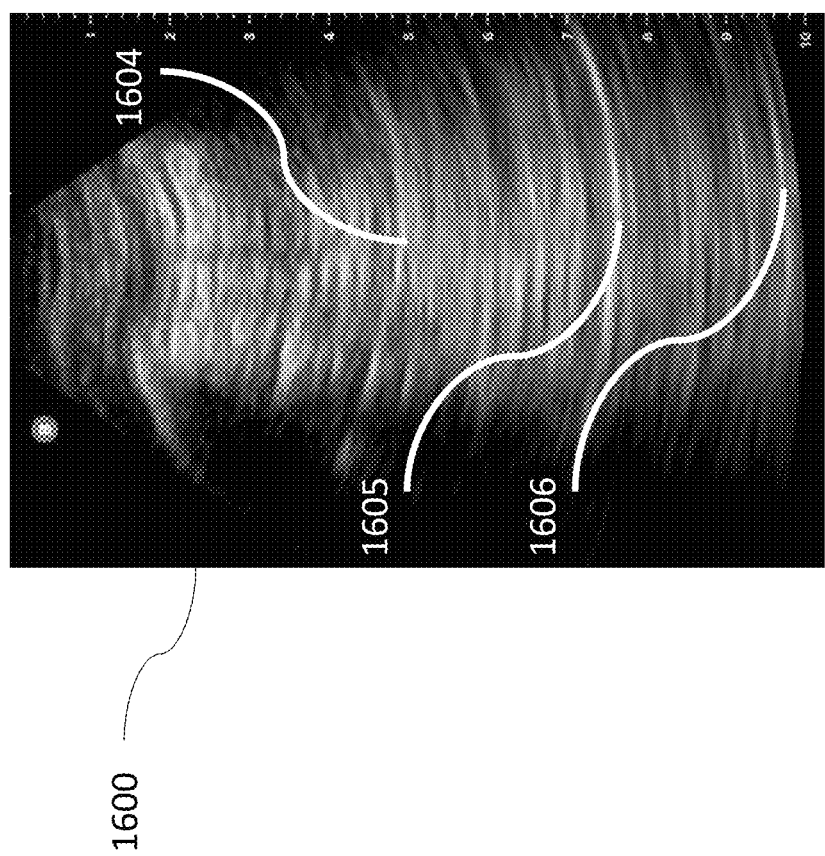
FIG. 16 illustrates an ultrasound image of the lungs collected using the same ultrasound probe as in FIG. 15 and a deep lung imaging mode, in accordance with certain embodiments described herein.

FIG. 16 illustrates an ultrasound image 1600 of the lungs collected using the same ultrasound device as in FIG. 15 and a deep lung imaging mode, in accordance with certain embodiments described herein. The ultrasound image 1600 was collected using an imaging depth of 10 cm. Multiple A lines 1604-1606 are visible in the ultrasound image 1600. It should be emphasized again that the ultrasound images 1500 and 1600, respectively depicting the lung pleura in high detail and multiple A lines, were collected with the same ultrasound device.

Figure 17:
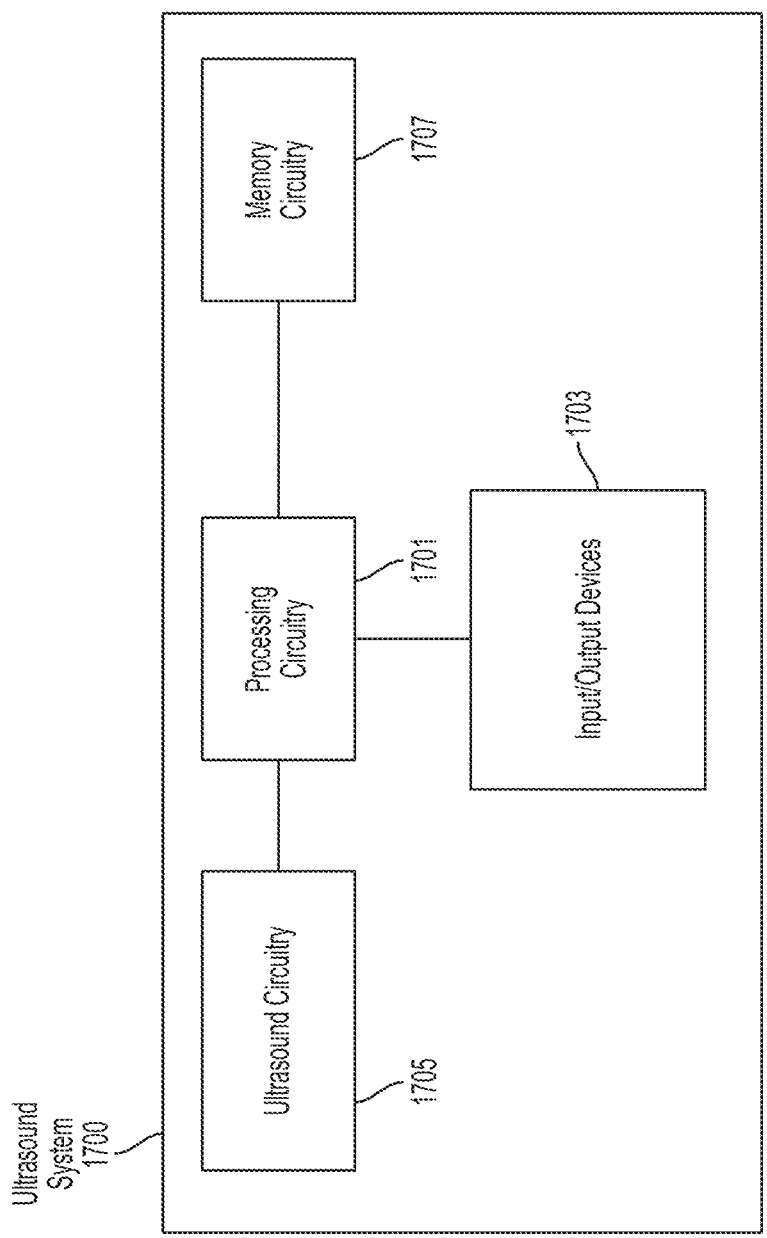
FIG. 17 shows a schematic block diagram illustrating aspects of an example ultrasound system upon which various aspects of the technology described herein may be practiced.

FIG. 17 shows a schematic block diagram illustrating aspects of an example ultrasound system 1700 upon which various aspects of the technology described herein may be practiced. For example, one or more components of the ultrasound system 1700 may perform any of the processes (e.g., the processes 100, 200, 300, and 400) described herein. As shown, the ultrasound system 1700 includes processing circuitry 1701, input/output devices 1703, ultrasound circuitry 1705, and memory circuitry 1707.

The ultrasound circuitry 1705 may be configured to generate ultrasound data that may be employed to generate an ultrasound image. The ultrasound circuitry 1705 may include one or more ultrasonic transducers monolithically integrated onto a single semiconductor die. The ultrasonic transducers may include, for example, one or more capacitive micromachined ultrasonic transducers (CMUTs), one or more CMOS ultrasonic transducers (CUTs), one or more piezoelectric micromachined ultrasonic transducers (PMUTs), and/or one or more other suitable ultrasonic transducer cells. In some embodiments, the ultrasonic transducers may be formed on the same chip as other electronic components in the ultrasound circuitry 1705 (e.g., transmit circuitry, receive circuitry, control circuitry, power management circuitry, and processing circuitry) to form a monolithic ultrasound device.

The processing circuitry 1701 may be configured to perform any of the functionality described herein. The processing circuitry 1701 may include one or more processors (e.g., computer hardware processors). To perform one or more functions, the processing circuitry 1701 may execute one or more processor-executable instructions stored in the memory circuitry 1707. The memory circuitry 1707 may be used for storing programs and data during operation of the ultrasound system 1700. The memory circuitry 1707 may include one or more storage devices such as non-transitory computer-readable storage media. The processing circuitry 1701 may control writing data to and reading data from the memory circuitry 1707 in any suitable manner.

In some embodiments, the processing circuitry 1701 may include specially-programmed and/or special-purpose hardware such as an application-specific integrated circuit (ASIC). For example, the processing circuitry 1701 may include one or more graphics processing units (GPUs) and/or one or more tensor processing units (TPUs). TPUs may be ASICs specifically designed for machine learning (e.g., deep learning). The TPUs may be employed to, for example, accelerate the inference phase of a neural network.

The input/output (I/O) devices 1703 may be configured to facilitate communication with other systems and/or an operator. Example I/O devices 1703 that may facilitate communication with an operator include: a keyboard, a mouse, a trackball, a microphone, a touch-enabled screen, a printing device, a display screen, a speaker, and a vibration device. Example I/O devices 1703 that may facilitate communication with other systems include wired and/or wireless communication circuitry such as BLUETOOTH, ZIGBEE, Ethernet, WiFi, and/or USB communication circuitry.

It should be appreciated that the ultrasound system 1700 may be implemented using any number of devices. For example, the components of the ultrasound system 1700 may be integrated into a single device. In another example, the ultrasound circuitry 1705 may be integrated into an ultrasound device that is communicatively coupled with a processing device that includes the processing circuitry 1701, the input/output devices 1703, and the memory circuitry 1707.

Figure 18:
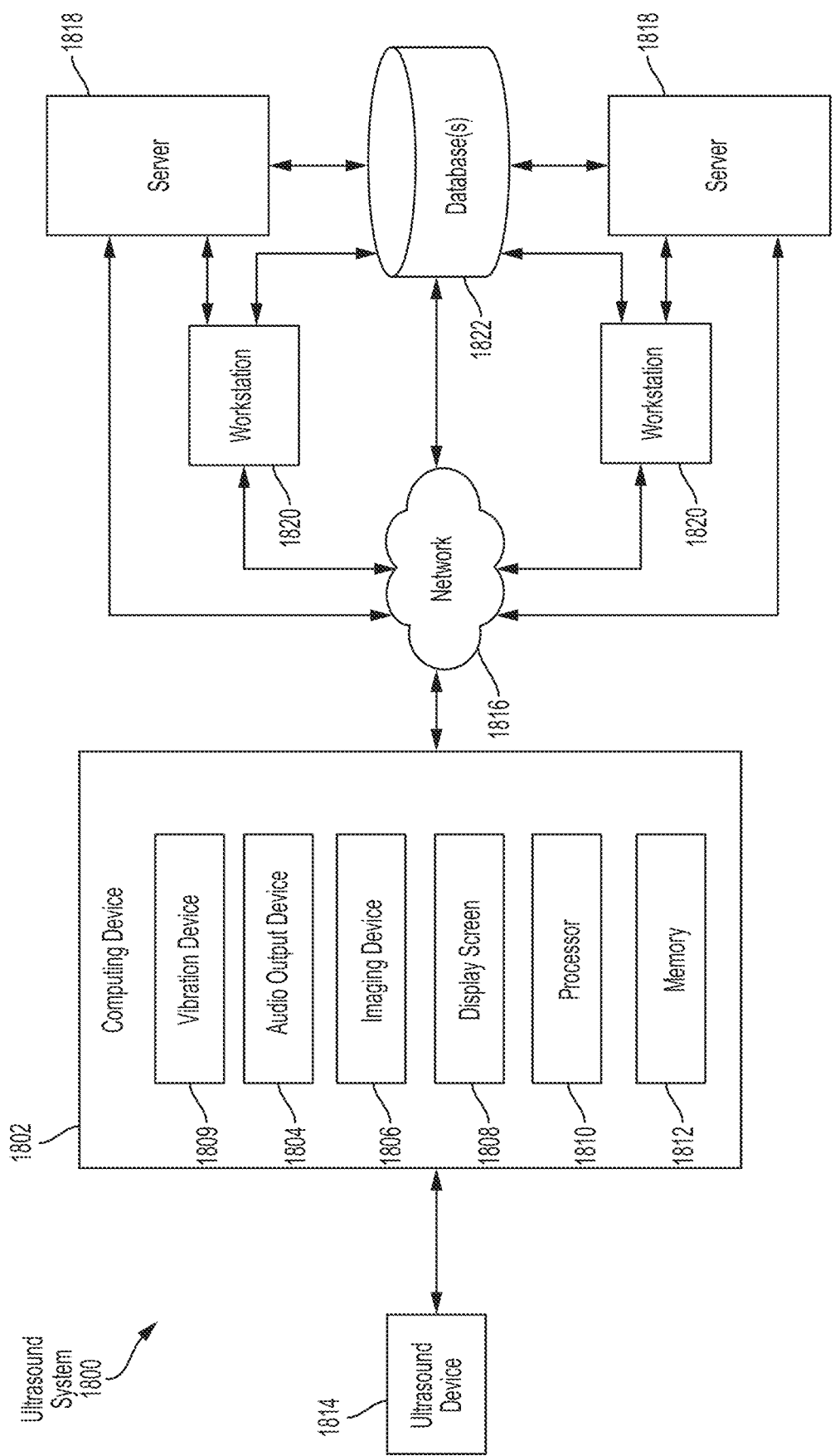
FIG. 18 shows a schematic block diagram illustrating aspects of another example ultrasound system upon which various aspects of the technology described herein may be practiced.

FIG. 18 shows a schematic block diagram illustrating aspects of another example ultrasound system 1800 upon which various aspects of the technology described herein may be practiced. For example, one or more components of the ultrasound system 1800 may perform any of the processes (e.g., the processes 100, 200, 300, and 400) described herein. As shown, the ultrasound system 1800 includes an ultrasound device 1814 in wired and/or wireless communication with a processing device 1802. The processing device 1802 includes an audio output device 1804, an imaging device 1806, a display screen 1808, a processor 1810, a memory 1812, and a vibration device 1809. The processing device 1802 may communicate with one or more external devices over a network 1816. For example, the processing device 1802 may communicate with one or more workstations 1820, servers 1818, and/or databases 1822.

The ultrasound device 1814 may be configured to generate ultrasound data that may be employed to generate an ultrasound image. The ultrasound device 1814 may be constructed in any of a variety of ways. In some embodiments, the ultrasound device 1814 includes a transmitter that transmits a signal to a transmit beamformer which in turn drives transducer elements within a transducer array to emit pulsed ultrasonic signals into a structure, such as a patient. The pulsed ultrasonic signals may be back-scattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data.

The processing device 1802 may be configured to process the ultrasound data from the ultrasound device 1814 to generate ultrasound images for display on the display screen 1808. The processing may be performed by, for example, the processor 1810. The processor 1810 may also be adapted to control the acquisition of ultrasound data with the ultrasound device 1814. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

Additionally (or alternatively), the processing device 1802 may be configured to perform any of the processes (e.g., the processes 100, 200, 300, and 400) described herein (e.g., using the processor 1810). As shown, the processing device 1802 may include one or more elements that may be used during the performance of such processes. For example, the processing device 1802 may include one or more processors 1810 (e.g., computer hardware processors) and one or more articles of manufacture that include non-transitory computer-readable storage media such as the memory 1812. The processor 1810 may control writing data to and reading data from the memory 1812 in any suitable manner. To perform any of the functionality described herein, the processor 1810 may execute one or more processor-executable instructions stored in one or more non-transitory computer-readable storage media (e.g., the memory 1812), which may serve as non-transitory computer-readable storage media storing processor-executable instructions for execution by the processor 1810.

In some embodiments, the processing device 1802 may include one or more input and/or output devices such as the audio output device 1804, the imaging device 1806, the display screen 1808, and the vibration device 1809. The audio output device 1804 may be a device that is configured to emit audible sound such as a speaker. The imaging device 1806 may be a camera configured to detect light (e.g., visible light) to form an optical image. The display screen 1808 may be configured to display images and/or videos such as a liquid crystal display (LCD), a plasma display, and/or an organic light emitting diode (OLED) display. The display screen 1808 may be a touch-enabled screen display. The vibration device 1809 may be configured to vibrate one or more components of the processing device 1802 to provide tactile feedback. These input and/or output devices may be communicatively coupled to the processor 1810 and/or under the control of the processor 1810. The processor 1810 may control these devices in accordance with a process being executed by the process 1810 (such as the processes 100, 200, 300, and 400).

It should be appreciated that the processing device 1802 may be implemented in any of a variety of ways. For example, the processing device 1802 may be implemented as a handheld device such as a mobile smartphone or a tablet. Thereby, an operator of the ultrasound device 1814 may be able to operate the ultrasound device 1814 with one hand and hold the processing device 1802 with another hand. In other examples, the processing device 1802 may be implemented as a portable device that is not a handheld device such as a laptop. In yet other examples, the processing device 1802 may be implemented as a stationary device such as a desktop computer.

In some embodiments, the processing device 1802 may communicate with one or more external devices via the network 1816. The processing device 1802 may be connected to the network 1816 over a wired connection (e.g., via an Ethernet cable) and/or a wireless connection (e.g., over a WiFi network). As shown in FIG. 18, these external devices may include servers 1818, workstations 1820, and/or databases 1822. The processing device 1802 may communicate with these devices to, for example, off-load computationally intensive tasks. For example, the processing device 1802 may send an ultrasound image over the network 1816 to the server 1818 for analysis (e.g., to identify an anatomical feature in the ultrasound) and receive the results of the analysis from the server 1818. Additionally (or alternatively), the processing device 1802 may communicate with these devices to access information that is not available locally and/or update a central information repository. For example, the processing device 1802 may access the medical records of a subject being imaged with the ultrasound device 1814 from a file stored in the database 1822. In this example, the processing device 1802 may also provide one or more captured ultrasound images of the subject to the database 1822 to add to the medical record of the subject. For further description of ultrasound devices and systems, see U.S. patent application Ser. No. 15/415,434 titled "UNIVERSAL ULTRASOUND PROBE AND RELATED APPARATUS AND METHODS," filed on Jan. 25, 2017 (and assigned to the assignee of the instant application), which is incorporated by reference herein in its entirety.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps In some embodiments describing ranges of values, such as the ranges of imaging depths in which the shallow vs. the deep lung imaging mode are selected, a first range of values may be less than or equal to a threshold value and a second range may be greater than the threshold value. It should be understood that the range encompassing the threshold value is non-limiting, and in other embodiments the first range may be less than the value and the second range may be greater than or equal to the value. Similarly, in embodiments in which a first range of values may be less than a threshold value and a second range may be greater than or equal to the threshold value, it should be understood that in other embodiments the first range may be less than or equal to the value and the second range may be greater than the value.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An apparatus, comprising:
a processing device in operative communication with an ultrasound device with exactly a single transducer array, the processing device configured to:
receive a user selection of a lung imaging preset option and a user-selected imaging depth for the ultrasound device;
define a threshold imaging depth based on a shallow lung imaging mode and a deep lung imaging mode, wherein the threshold imaging depth is between approximately 4 cm and 8 cm;
after receiving the user selection of the user-selected imaging depth, compare the user-selected imaging depth with the threshold imaging depth; and
automatically configure the single transducer array of the ultrasound device to switch between the shallow lung imaging mode and the deep lung imaging mode, depending upon a result of the comparison of the user-selected imaging depth with the threshold imaging depth, wherein
the shallow lung imaging mode comprises a peak frequency of transmitted ultrasound between approximately 5 MHz and 10 MHz, and
the deep lung imaging mode comprises a peak frequency of transmitted ultrasound between approximately 2 MHz and 5 MHz.

2. The apparatus of claim 1, wherein:
the shallow lung imaging mode is associated with imaging depths that are smaller than or equal to the threshold imaging depth and the deep lung imaging mode is associated with imaging depths that are larger than the threshold imaging depth; or
the shallow lung imaging mode is associated with imaging depths that are smaller than the threshold imaging depth and the deep lung imaging mode is associated with imaging depths that are larger than or equal to the threshold imaging depth.

3. The apparatus of claim 1, wherein
the shallow lung imaging mode comprises a receive frequency between approximately 5 MHz and 10 MHz.

4. The apparatus of claim 1, wherein
the deep lung imaging mode comprises a receive frequency between approximately 2 MHz and 5 MHz.

5. The apparatus of claim 1, wherein
the shallow lung imaging mode comprises a virtual apex greater than or equal to approximately 10 cm above a skin line of a subject being imaged.

6. The apparatus of claim 1, wherein
the deep lung imaging mode comprises a virtual apex between approximately 0 cm and 5 cm above a skin line of a subject being imaged.

7. The apparatus of claim 1, wherein
the shallow lung imaging mode comprises an image field of view angle between approximately 0 and 20 degrees around a virtual apex.

8. The apparatus of claim 1, wherein
the deep lung imaging mode comprises an image field of view angle between approximately 40 degrees and 90 degrees around a virtual apex.

9. The apparatus of claim 1, wherein
the shallow lung imaging mode comprises an instantaneous transmit aperture between approximately 4 mm and 8 mm.

10. The apparatus of claim 1, wherein
the deep lung imaging mode comprises an instantaneous transmit aperture between approximately 12 mm and 20 mm.

11. The apparatus of claim 1, wherein
the shallow lung imaging mode comprises a linear ultrasound image format.

12. The apparatus of claim 1, wherein
the deep lung imaging mode comprises a sector ultrasound image format.

13. The apparatus of claim 1, wherein
the shallow lung imaging mode comprises time gain compensation gain values of approximately 0 dB, −8 dB, and −2 dB at respective control points of approximately 0 cm, 3 cm, and 6 cm.

14. The apparatus of claim 1, wherein
the deep lung imaging mode comprises time gain compensation gain values of approximately 0 dB, 0 dB, and 5 dB at respective control points of approximately 0 cm, 3 cm, and 6 cm.

15. The apparatus of claim 1, wherein
the shallow lung imaging mode is optimized for imaging lung sliding.

16. The apparatus of claim 1, wherein
the deep lung imaging mode is optimized for imaging A lines and B lines.

17. The apparatus of claim 1, wherein
the processing device is further configured to automatically determine that lung imaging is being performed by the ultrasound device.

18. The apparatus of claim 17, wherein
the processing device is configured, when automatically determining that lung imaging is being performed by the ultrasound device, to:
receive ultrasound data from the ultrasound device; and
determine that the ultrasound data was collected from lungs.

19. The apparatus of claim 18, wherein
the processing device is configured, when determining that the ultrasound data was collected from the lungs, to input the ultrasound data to a statistical model trained to accept inputted ultrasound data and determine an anatomical region where the inputted ultrasound data was collected.

20. The apparatus of claim 17, wherein
the processing device is configured, when automatically determining that lung imaging is being performed by the ultrasound device, to
receive an optical image of the ultrasound device and a subject; and
determine that the ultrasound device is located at the subject's lungs.

21. The apparatus of claim 20, wherein
the processing device is configured, when determining that the ultrasound device is located at the subject's lungs, to input the ultrasound data to a statistical model trained to accept an inputted optical image depicting an ultrasound device and a subject and determine an anatomical region on the depicted subject where the depicted ultrasound device is located.

22. The apparatus of claim 20, wherein the optical image is collected by a camera on the processing device.

23. The apparatus of claim 1, wherein the user-selected imaging depth is a depth of a B-mode image.

* * * * *